(12) United States Patent
Hwang et al.

(10) Patent No.: US 7,902,254 B1
(45) Date of Patent: Mar. 8, 2011

(54) METHOD FOR TREATING CONDITIONS MEDIATED BY PPAR USING MACELIGNAN

(75) Inventors: Jae-Kwan Hwang, Gyeonggi-do (KR); Kyu-Lee Han, Seoul (KR); Jong-Hee Sohn, Seoul (KR); Ah-Jin Kim, Seoul (KR); Jeong-Han Choo, Gyeonggi-do (KR); Jae-Young Lee, Gyeonggi-do (KR); Jeong-Hwan Kim, Seoul (KR); Do Un Kim, Gyeonggi-do (KR); Heechul Chung, Gyeonggi-do (KR); Jae Youn Chung, Gyeonggi-do (KR)

(73) Assignee: Newtree Co., Ltd., Sungnam, Gyeonggi-Do (KR)

( * ) Notice: Subject to any disclaimer, the term of this patent is extended or adjusted under 35 U.S.C. 154(b) by 0 days.

(21) Appl. No.: 11/922,509

(22) PCT Filed: Jun. 27, 2006

(86) PCT No.: PCT/KR2006/002493
§ 371 (c)(1),
(2), (4) Date: Jan. 28, 2008

(87) PCT Pub. No.: WO2007/001150
PCT Pub. Date: Jan. 4, 2007

(30) Foreign Application Priority Data

Jun. 27, 2005 (KR) .................. 10-2005-0055539
Jun. 29, 2005 (KR) .................. 10-2005-0056692
Sep. 22, 2005 (KR) .................. 10-2005-0087991

(51) Int. Cl.
*A61K 31/36* (2006.01)
(52) U.S. Cl. ........................................ 514/464
(58) Field of Classification Search .......... 514/464
See application file for complete search history.

(56) References Cited

OTHER PUBLICATIONS

Shin et al (Arch. Pharm. Res., vol. 13, No. 3, pp. 265-268; 1990).*
Ram, V.J. ["Therapeutic role of peroxisome proliferator-activated receptors in obesity, diabetes and inflammation." in: Jucker, E., Progress in Drug Research (Switzerland, Birkhauser Verlag, Basel, 2003), pp. 93, 95 and 99-105].*
Kreijkamp-Kaspers et al (Journal of Hypertension, vol. 22, No. 7, pp. 1381-1388; 2004).*
Birrell et al (Eur Respir J, vol. 24, pp. 18-23; 2004).*
Sérée et al. (Gastroenterology, vol. 127, No. 5, Abstract; 2004).*
Roy et al. (Cancer Research, vol. 48, pp. 5726-5729; 1988).*
Merck Manual reference (Retrieved on Feb. 26, 2010 from the Internet: <URL: http://www.merck.com/mmhe/sec11/ch144/ch144b.html?qt=glomerulonephritis&alt=sh).*

* cited by examiner

*Primary Examiner* — Ardin Marschel
*Assistant Examiner* — Nelson C Blakely, III
(74) *Attorney, Agent, or Firm* — Buchanan Ingersoll & Rooney PC

(57) ABSTRACT

Disclosed is a method for treating PPAR (peroxisome proliferator activated receptor)-mediated diseases, such as diabetes mellitus, which includes administering to a subject an effective amount of macelignan represented by the following Formula (I):

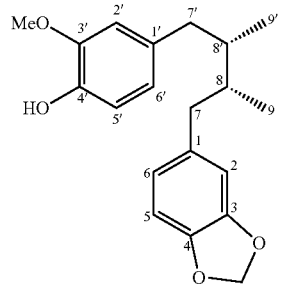

or a pharmaceutically acceptable salt thereof.

3 Claims, 19 Drawing Sheets

METHOD FOR TREATING CONDITIONS MEDIATED BY PPAR USING MACELIGNAN

TECHNICAL FIELD

The present invention relates to a method for treating conditions mediated by PPAR, which comprises administering an effective amount of macelignan or a pharmaceutically acceptable salt thereof to a subject.

BACKGROUND ART

PPAR (peroxisome proliferator activated receptor) refers to an intranuclear receptor whose ligand is a peroxisome proliferator, a compound capable of increasing the number of peroxisome. Also, it is known that PPAR has three isoforms of PPARα, PPARδ and PPARγ (*J Steroid Biochem. Molec. Biol.*, 51, 157, 1994; *Gene Expression*, 4, 281, 1995; *Biochem. Biophys. Res. Commun.*, 224, 431, 1996).

PPAR mainly controls expression of genes participating in fat metabolism or genes participating in differentiation of adipocytes (*J. Invest. Dermatol.* 111, 1116-1121, 1998; *J. Med. Chem.*, 43, 527-550, 2000). Among the above PPAR isoforms, PPARα is expressed mainly in the liver, the retina and the adipose tissue, and participates in oxidation of fatty acids, neutralization of toxic materials, or inflammatory reactions. PPARγ is expressed mainly in the adipocytes, the immune cells, the adrenal gland, the spleen and the small intestine, and is known to function as a central mediator in the differentiation of adipocytes. PPARδ is not expressed in a tissue-specific manner but expressed broadly, and the function of PPARδ is not clearly understood (*Endocrinology.*, 137, 354, 1996).

Because PPAR has an important role in fat metabolism, many studies have been conducted to develop a medicine for treating metabolic diseases in which PPAR is involved. It is known that when PPARα is activated, expression of enzymes increasing fatty acid decomposition and decreasing fatty acid synthesis in the liver increases, thereby decreasing synthesis of triglycerides and production and secretion of VLDL (very low density lipoprotein). It is also known that activation of PPARα result in activation of LPL (lipoprotein lipase), and reduced production of apoC-III which is inducing generation of VLDL (*Curr. Pharm Des.*, 3: 1-14, 1997). Additionally, it is known that fibrate, known as a ligand of PPARα, reduces triglycerides by 20-50%, and reduces LDL while increasing HDL (*Atherosclerosis*, 171: 1-13, 2003). Therefore, ligands of PPARα are useful for treating obesity, dyslipidemia and cardiovascular diseases caused by accumulation of triglycerides (*Curr. Opin. Lipidol.*, 10: 245-257, 1999).

In addition, activation of PPARγ causes maximization of sugar receptability of adipocytes, stimulates differentiation of adipocytes and reduces insulin resistance (*Tren. Pharmacol. Sci.*, 25:331-336, 2004). Therefore, ligands of PPARγ can act as medicine for treating non-insulin-dependent diabetes mellitus (Type 2 diabetes mellitus) caused by insulin resistance. Currently, TZD pharmaceuticals such as pioglitazone and rosiglitazone, which are typical ligands of PPARγ, are used as medicines for treating non-insulin-dependent diabetes mellitus.

As mentioned above, since PPAR is a target in the treatment of metabolic diseases including diabetes, diabetic complications, or the like, many attempts have been made to date to develop PPAR ligands for activating PPAR. U.S. Pat. No. 6,939,875 discloses a composition useful for treating PPAR-mediated diseases. It is also disclosed that the composition of U.S. Pat. No. 6,939,875 is effective for treating non-insulin-dependent diabetes mellitus, obesity, eating disorders, appetite suppressing, leptin level modulation, and metabolic syndrome. Additionally, U.S. Pat. No. 6,967,212 discloses a composition comprising a substituted azole acid derivative acting as a PPAR agonist. It is also disclosed that the composition of U.S. Pat. No. 6,967,212 is effective for treating insulin resistance, hyperglycemia, hyperinsulinemia, hyperlipidemia, obesity, syndrome X, dysmetabolic syndrome, inflammation, diabetic complications, impaired glucose homeostasis, impaired glucose tolerance, hypertriglyceridemia or atherosclerosis. Further, other substances effective for treating various PPAR-mediated diseases are disclosed (U.S. Pat. Nos. 6,930,120, 7,041,691 and 7,037,914).

However, PPAR ligands that have been known to date cause side effects such as liver toxicity, hypoglycemic conditions and obesity. Hence, it is required to develop a ligand capable of activating PPAR from a natural source that causes low side effects such as toxicity. Nevertheless, there have been few studies to develop a ligand capable of activating PPAR from a natural source.

Meanwhile, *Myristica fragrans* is a perennial plant cultivated in the tropics. Fruits of *Myristica fragrans*, known as mace or nutmeg, have been used as spice for a long time. Macelignan is a typical lignan-based compound, which is found in *Myristica fragrans* (*Phytochemistry*, 59: 169-17, 2002). It is reported that macelignan has the functions of enhanced activity of caspase-3 inducing apoptosis (*Biol. Pharm. Bull.*, 27: 1305-1307, 2004), an antibacterial effect against oral microorganisms (Korean Laid-Open Patent No. 10-2005-0035954), inhibited peroxidation of cerebral cell lipids and inhibited production of active oxygen (*Biochem. Biophys. Res. Commu.*, 331: 1264-1269), or the like. However, any studies of the interrelation between macelignan and PPAR have not yet been reported.

DISCLOSURE OF THE INVENTION

Therefore, the inventors of the present invention have conducted intensive studies to search for a substance effective for treating PPAR-mediated diseases, such as diabetes mellitus, diabetic complications, obesity or hyperlipidemia, from various natural sources. Finally, we have found that macelignan isolated from *Myristica fragrans* is effective for activating PPAR, and thus for treating PPAR-mediated diseases. The present invention is based on this finding.

Therefore, it is an object of the present invention to provide a method for treating PPAR-mediated diseases, which comprises administering an effective amount of macelignan or a pharmaceutically acceptable salt thereof to a subject.

In order to accomplish the above object, the present invention provides a method for treating PPAR-mediated diseases, which comprises administering an effective amount of macelignan or a pharmaceutically acceptable salt thereof to a subject.

Hereinafter, the present invention will be explained in more detail.

According to the present invention, the method for treating PPAR-mediated diseases comprises administering an effective amount of macelignan represented by the following Formula (I) or a pharmaceutically acceptable salt thereof to a subject.

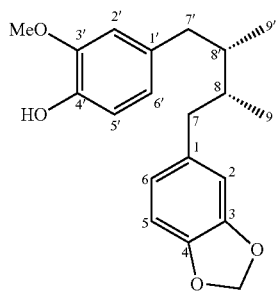

[Formula I]

Macelignan used in the method according to the present invention is commercially available or may be isolated and purified from a natural source. Otherwise, macelignan may be prepared by a chemical synthetic process known to those skilled in the art.

Preferably, macelignan used in the method according to the present invention may be isolated and purified from a natural source. More preferably, macelignan may be isolated and purified from *Myristica fragrans*, and most preferably from nutmeg or aril of *Myristica fragrans*. Additionally, macelignan may be isolated and purified from other myristicaceae plants, such as *Myristica argentea* Warb (*Nat. Prod. Lett.*, 16: 1-7, 2002), Machilus thunbergii (*Bio. Pharm. Bull.*, 27: 1305-1307, 2004), or *Leucas aspera* (*Chem. Pharm. Bull.*, 51: 595-598, 2003).

Preferably, macelignan used in the present invention may be isolated and purified from nutmeg via a separation process using solvent extraction and chromatography which are known in the art.

For example, extraction of macelignan from nutmeg may be carried out by using any one solvent selected from the group consisting of water, organic solvents including C1~C6 alcohols, such as ethanol, methanol, propanol, isopropanol and butanol, acetone, ether, chloroform, ethyl acetate, methylene chloride, hexane, cyclohexane, petroleum ether, diethyl ether, and benzene, or a mixed solvent thereof. Preferably, such extraction may be performed by using water or a C1~C6 alcohol. Most preferably, macelignan used in the present invention may be extracted by using methanol as a solvent.

For extraction, methanol may be added to nutmeg powder in an amount of 1~20 times (on the weight basis) of the amount of nutmeg powder, but not limited thereto. Preferably, methanol may be added to nutmeg powder in an amount of 2~5 times (on the weight basis) of the amount of nutmeg powder in order to increase extraction efficiency.

Extraction of nutmeg is performed preferably at room temperature under ambient pressure. Although extraction time depends on extraction temperature, extraction is performed generally for 6~96 hours, and preferably for 36~72 hours. Additionally, extraction using a shaker may further increase extraction efficiency.

Nutmeg is used in the extraction, after it is collected and washed, and optionally dried. As a drying process, a sun drying process, a shade drying process, a hot air drying process or a natural drying process may be used. Additionally, in order to increase extraction efficiency, nutmeg or a dried product thereof may be pulverized in a mill.

Isolation of macelignan from the extract can be performed by using a separation process based on chromatography generally known to those skilled in the art. For example, the extract is loaded to a silica gel column chromatography to obtain different fractions having different levels of polarity, and then a specific fraction is further subjected to reverse phase column chromatography and high performance liquid chromatography (HPLC) to isolate macelignan.

According to a preferred embodiment, extraction of macelignan used in the present invention is performed by pulverizing dried nutmeg into a size of 20~40 mesh, and adding methanol thereto in an amount of three times of the amount of nutmeg powder to carry out extraction for 48 hours at room temperature. The extract obtained as described above is centrifuged, the precipitate is removed, and the supernatant is collected to obtain nutmeg extract containing macelignan. Then, the nutmeg extract is fractionated into an ethyl acetate layer, a butanol layer and a water layer, and the ethyl acetate layer is subjected to a silica gel column and eluted with hexane and ethyl acetate (10:1 (v/v)) to obtain a desired fraction. The fraction is further subjected to a silica gel column and eluted with hexane and ethyl acetate (20:1 (v/v)) to obtain a desired fraction, which, in turn, is subjected to a RP-18 column and eluted with 80% methanol to obtain isolated macelignan.

Macelignan used in the method of the present invention acts as a ligand to PPAR, thereby activating PPAR. This has been demonstrated by the inventors of the present invention for the first time.

According to an embodiment of the present invention, it has been found that macelignan used in the present invention is bound to PPAR, particularly PPARα and PPARγ, thereby activating PPAR, through a known method for detecting a ligand capable of being bound to PPAR to activate genes having the PPAR response element (PPRE).

When PPAR is activated, it is bound to a DNA sequence referred to as PPRE (PPAR response element) to control the expression of target genes. Mainly, expression of target genes of PPAR involved in fat metabolism increases. Therefore, according to another embodiment of the present invention, macelignan has been investigated as to whether it increases expression of CD36, CPT-1, PDK 4, ACO, LPL and PEPCK, known as target genes of PPAR. As a result, it was shown that treatment with macelignan significantly increases expression of the target genes of PPAR.

Meanwhile, it is known that as PPAR is activated, sugar receptability of adipocytes is maximized and the differentiation of adipocytes is stimulated (*Trends in Pharmacological Sciences*, 25: 331-336, 2004). Therefore, according to still another embodiment of the present invention, macelignan has been investigated as to whether it activates PPAR to stimulate the differentiation of adipocytes. As a result, it was shown that macelignan used in the present invention can stimulate differentiation of 3T3-L1, pre-adipocytes (see FIG. 10).

According to still another embodiment of the present invention, it was shown that macelignan has the effect of treating or preventing obesity, hyperlipidemia and cardiovascular diseases caused by obesity by reducing body weight significantly in an obesity/diabetes mouse model. Additionally, according to yet another embodiment of the present invention, it was demonstrated that macelignan has the effect of treating or preventing non-insulin-dependent diabetes mellitus by reducing blood sugar significantly in an obesity/diabetes mouse model.

In brief, it can be seen that macelignan is a ligand of PPARα that increases fat decomposition and of PPARγ that increases insulin sensitivity, has the use for inhibiting obesity and metabolic diseases including hyperlipidemia and cardiovascular disease by significantly reducing body weight and triglycerides in blood in an obesity/diabetes model, and shows the use for inhibiting non-insulin-dependent diabetes mellitus by reducing blood sugar in the same model.

Therefore, macelignan is useful for a method for treating PPAR-mediated diseases.

As used herein, "PPAR-mediated diseases" refer to diseases or conditions of which are prevented, treated, reduced and alleviated by the activation of PPAR. Preferably, PPAR-mediated diseases include: NIDDM (non-insulin-dependent diabetes mellitus), hyperinsulinemia, obesity, hyperglycemia, hyperlipidemia, syndrome X, hypercholesterolemia, hyperlipoproteinemia, atherosclerosis, hypertension, insulin resistance, dysmetablic syndrome, diabetic complications, impaired glucose homeostasis, impaired glucose tolerance, hypertriglyceridemia, osteoporosis (*J. Biol. Chem.* 275: 14388-14393, 2000), glomerulonephritis (*Kidney Int.*, 14-30, 2001), or diabetic nephropathia (*Kidney Int.*, 60: 14-30, 2001).

The method for treating PPAR-mediated diseases according to the present invention comprises administering an effective amount of a composition having macelignan or a pharmaceutically acceptable salt thereof to a subject. Herein, the term "effective amount" means such an amount that a response higher than the response of the negative control can be obtained, and preferably an amount sufficient to treat or prevent PPAR-mediated diseases. The effective amount of composition having macelignan or a pharmaceutically acceptable salt according to the present invention is 0.1~200 mg/day/kg (body weight), preferably 1~30 mg/day/kg (body weight), but is not limited thereto. However, the effective amount is determined considering various factors, including disease and disease severity, age, body weight, health, sex, diet and excretion of a patient, administration route, administration period, frequency of treatment, and combination of other drugs. In addition, the term "subject" refers to a mammal in need of treatment or prevention of PPAR-mediated diseases, preferably, a human.

According to the present invention, macelignan may be used in the form of a salt, preferably a pharmaceutically acceptable salt. Preferably, the salt includes an acid addition salt formed with a pharmaceutically acceptable free acid. Such free acids include organic acids and inorganic acids. Particular examples of the organic acids include, but are not limited to: citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluene sulfonic acid, glutamic acid and aspartic acid. Additionally, particular examples of the inorganic acids include, but are not limited to: hydrochloric acid, hydrobromic acid, sulfuric acid and phosphoric acid.

Hereinabove, the term "pharmaceutically acceptable" refers to substances that are physiologically acceptable have no inhibitory effect of active ingredients, and cause no allergic reactions or similar reactions, such as gastrointestinal disorders or fainting, when administered to a human or an animal.

Meanwhile, according to the present invention, macelignan or a pharmaceutically acceptable salt thereof may be formulated with a carrier suitable for the particular administration route. Such carriers include all kinds of solvents, dispersing agent, oil-in-water or water-in-oil emulsion, aqueous compositions, liposomes, microbeads and microsomes. Administration routes of the pharmaceutical composition according to the present invention include, but are not limited to, oral or parenteral routes. Particular examples of parenteral administration routes include transdermal, nasal, intraperitoneal, intramuscular, subcutaneous or intravenous routes.

When macelignan or a pharmaceutically acceptable salt thereof according to the present invention is orally administered, it may be formulated into the form of powder, granules, tablets, pills, sugar-coated tablets, capsules, liquid, gel, syrup, suspension, wafer, or the like, together with a suitable carrier for oral administration by using a process known to those skilled in the art. Particular examples of suitable carriers include: saccharides, such as lactose, dextrose, sucrose, sorbitol, mannitol, xylitol, erythritol and maltitol; starch, such as corn starch, wheat starch, rice starch and potato starch; cellulose, such as methyl cellulose, sodium carboxymethyl cellulose and hydroxypropylmethyl cellulose; and fillers, such as gelatin, polyvinyl pyrrolidone, or the like. If necessary, it is possible to further add a disintegrating agent, such as a crosslinking agent, polyvinyl pyrrolidone, agar, alginic acid or sodium alginate. In addition, the pharmaceutical composition according to the present invention may further comprise an anti-agglomerating agent, a lubricant, a wetting agent, a fragrance agent and a preservative.

Meanwhile, when macelignan or a pharmaceutically acceptable salt thereof is administered via a parenteral route, it may be formulated into the form of a composition for injection, transdermal administration or nasal inhalation, together with a carrier suitable for parenteral administration by using a process generally known to those skilled in the art. In the case of a composition for injection, it is necessary to sterilize the composition and to protect the composition from being contaminated with microorganisms such as bacteria and fungi. Particular examples of the carriers suitable for injection administration include, but are not limited to: water, ethanol, polyol (e.g. glycerol, propylene glycol and liquid polyethylene glycol), a mixture thereof and/or a solvent or dispersion medium containing vegetable oil. More preferably, suitable carriers include Hanks' balanced salt solution, Ringer's solution, PBS (phosphate buffered saline) containing triethanol amine or sterilized water for injection, isotonic solution such as 10% ethanol, 40% propylene glycol or 5% dextrose, or the like. To protect the injection formulation from being contaminated with microorganisms, the formulation may further comprise various antibacterial agent and antifungal agent, such as paraben, chlorobutanol, phenol, sorbic acid, thimerosal, or the like. In most cases, an injection formulation may further comprise an isotonic agent such as sugar or sodium chloride.

Compositions for transdermal administration may be formulated into the form of ointment, cream, lotion, gel, solution for external use, pasta, liniment, aerosol, or the like. Herein, the term "transdermal administration" refers to local administration of a pharmaceutical composition on the skin, resulting in delivery of an effective amount of active component contained in the pharmaceutical composition into the skin. The above formulations are described in more detail in a textbook (*Remington's Pharmaceutical Science*, 15$^{th}$ Edition, 1975, Mack Publishing Company, Easton, Pa.), widely known in the field of pharmaceutical chemistry.

In the case of an inhalation formulation, the compound used in the method according to the present invention may be conveniently delivered in the form of an aerosol spray formulation from a pressurized pack or an atomizer by using a suitable propellant, such as dichlorofluoromethane, trichlorofluoromethane, dichlorotetrafluoroethane, carbon dioxide or other suitable gases. In the case of a pressurized aerosol, dosage unit may be determined by providing a valve capable of delivering a metered amount of drug. For example, a gelatin capsule or a cartridge used in an inhalator or insufflator may comprise a powder mixture containing the compound and a suitable powder base such as lactose or starch.

Other pharmaceutically acceptable carriers are described in more detail in [*Remington's Pharmaceutical Science, 19th* Edition, Mack Publishing Company. Easton, Pa., 1995].

Additionally, macelignan or a pharmaceutically acceptable salt thereof used in the method according to the present invention may further comprise at least one buffer (e.g. saline or PBS), carbohydrate (e.g. glucose, mannose, sucrose or dextran), antioxidant, bacteriostatic agent, chelating agent (e.g. EDTA or glutathione), adjuvant (e.g. aluminum hydroxide), suspending agent, thickening agent and/or preservative.

Meanwhile, macelignan or a pharmaceutically acceptable salt thereof may be formulated using known method in the art so as to provide rapid, durable or delayed release of the active component after the administration to a subject.

Further, according to the present invention, macelignan or a pharmaceutically acceptable salt thereof may be administered in combination with a known compound, such as TZD, having the effect of preventing or treating PPAR-mediated diseases.

After carrying out a toxicity test upon the oral administration of macelignan to rats, lethal dose 50% ($LD_{50}$) in an oral toxicity test was shown to be 2,000 mg/kg or more.

BRIEF DESCRIPTION OF THE DRAWINGS

The foregoing and other objects, features and advantages of the present invention will become more apparent from the following detailed description when taken in conjunction with the accompanying drawings in which.

BEST MODE FOR CARRYING OUT THE INVENTION

Reference will now be made in detail to the preferred embodiments of the present invention. It is to be understood that the following examples are illustrative only and the present invention is not limited thereto.

Example 1

Isolation and Purification of Macelignan from *Myristica fragrans*

<1-1> Isolation and Purification of Macelignan

Figure 1:
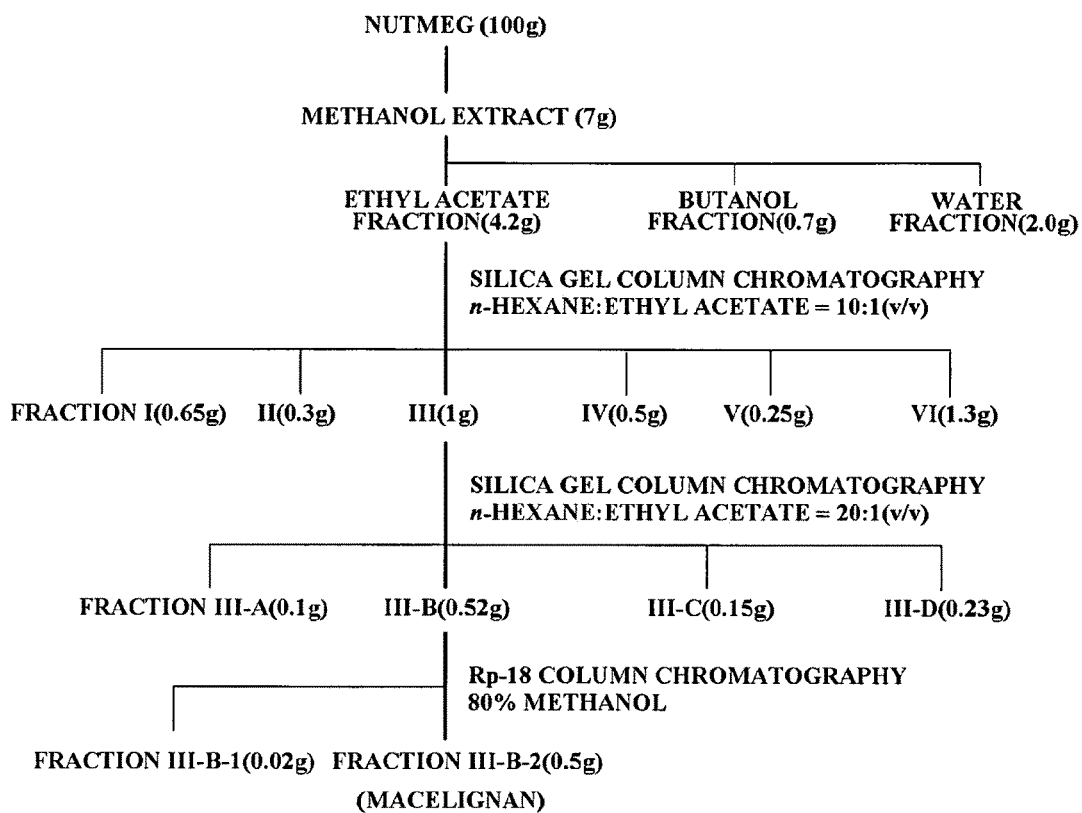
FIG. 1 is a flow chart of a process for isolating macelignan from nutmeg of *Myristica fragrans;*

To 100 g of dried and pulverized nutmeg, 400 ml of 75% methanol was added, and the mixture was left at room temperature for 2 days. The extracted solution was filtered and concentrated under vacuum to obtain methanol extract of nutmeg (7 g). Next, the extract was fractionated into an ethyl acetate layer, a butanol layer and a water layer, and each fraction was concentrated under vacuum to obtain an ethyl acetate fraction, a butanol fraction and a water fraction. The ethyl acetate fraction (4.2 g) was subjected to silica gel column chromatography (Merck Kieselgel 66; 70-230 mesh) using hexane and ethyl acetate (10:1 (v/v)) as an eluant to obtain fraction III (1 g). Additionally, fraction III was subjected to silica gel column chromatography (Merck Kieselgel 66; 70-230 mesh) using hexane and ethyl acetate (20:1 (v/v)) as an eluant to obtain fraction III-B (0.52 g). Then, fraction III-B was further subjected to Rp-18 column chromatography (Merck LiChroprep; 25-40 µm) using 80% methanol as an eluant to obtain a single substance, fraction III-B-2 (0.5 g). The above isolation process is shown in FIG. 1 in the form of a flow chart.

<1-2> Structural Analysis

Figure 2:
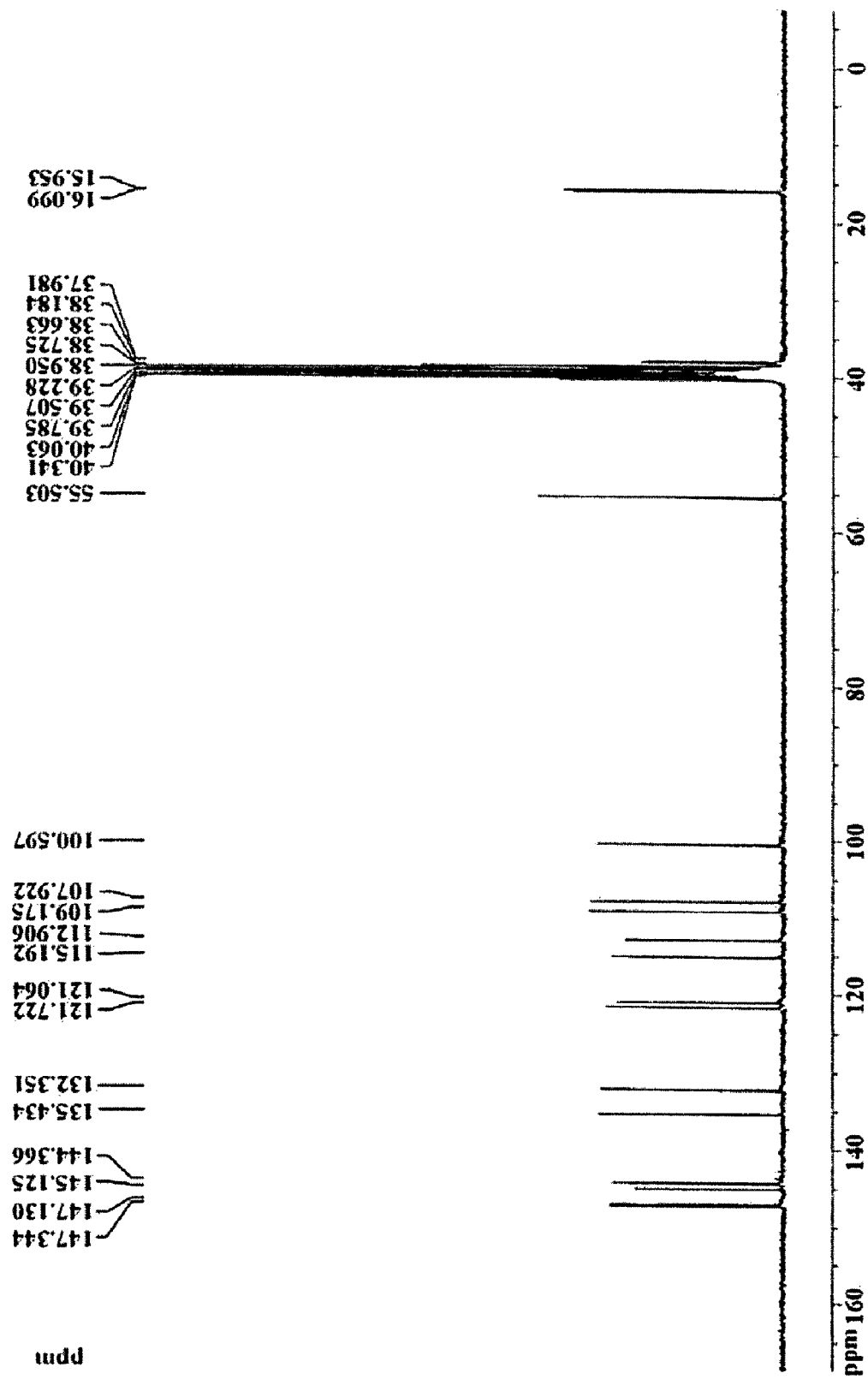
FIG. 2 is $^{13}C$-NMR spectrum of macelignan according to the present invention.
Figure 3:
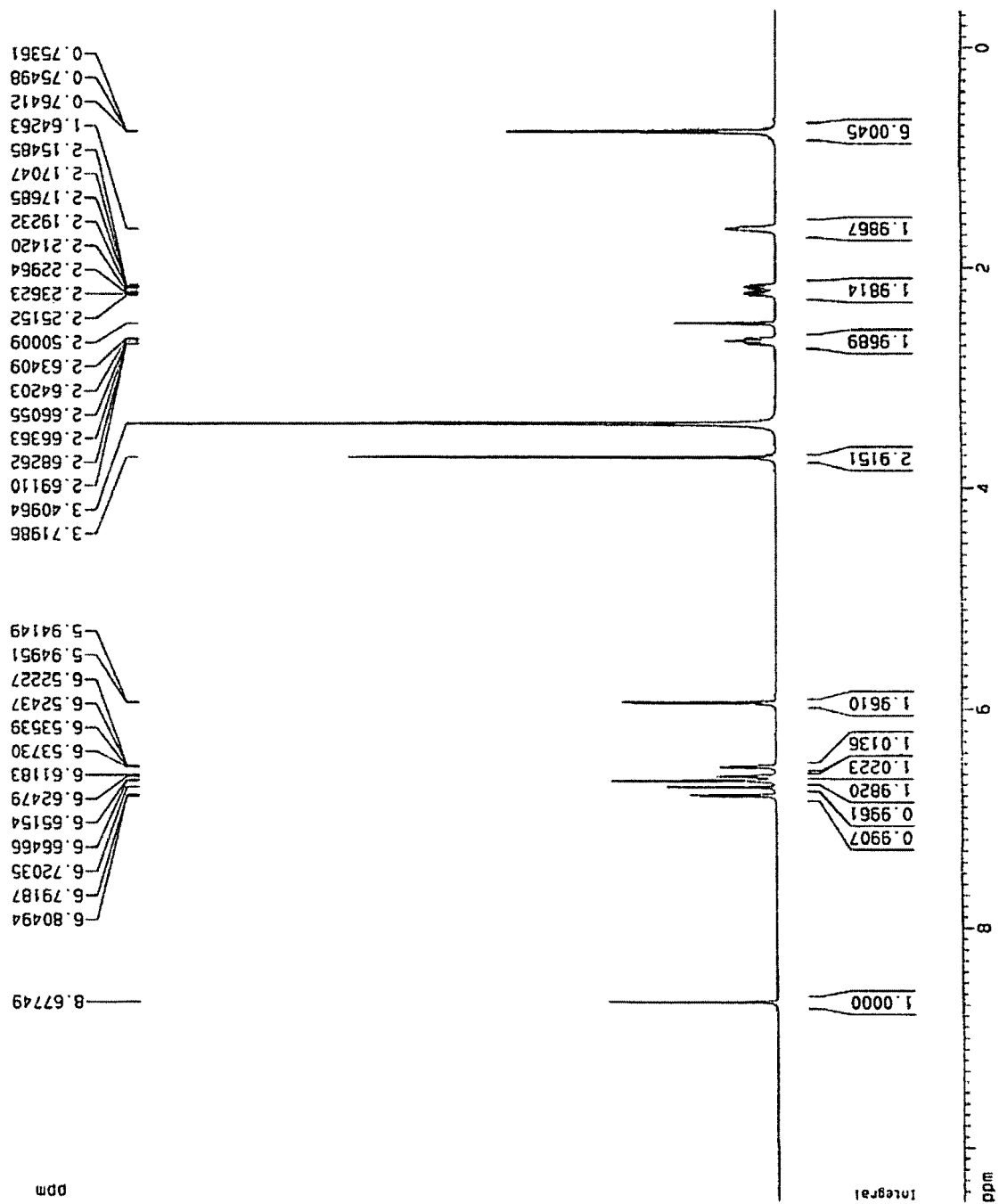
FIG. 3 is $^{1}H$-NMR spectrum of macelignan according to the present invention.
Figure 4:
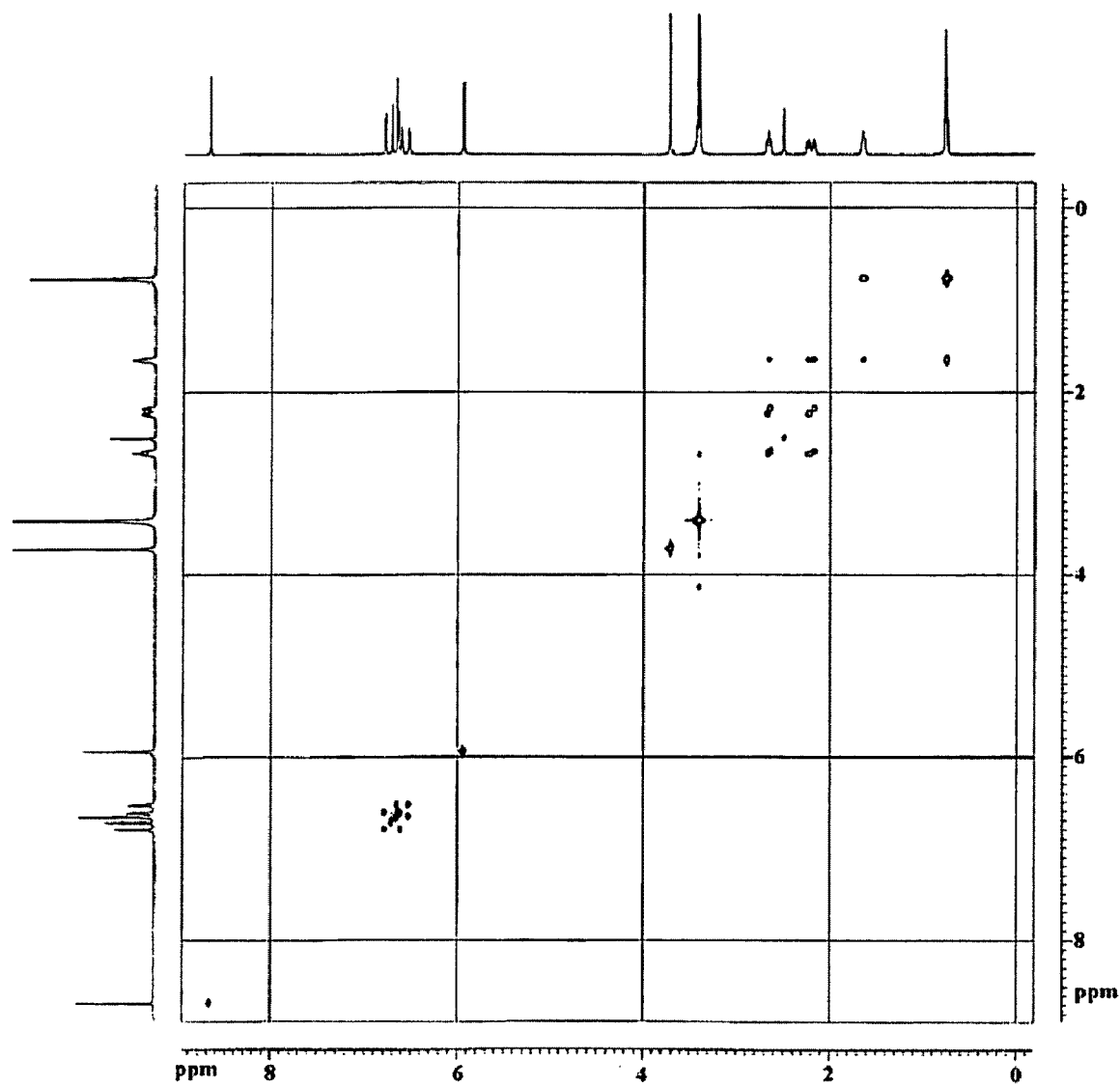
FIG. 4 is $^{1}H$-$^{1}H$ COSY spectrum of macelignan according to the present invention.
Figure 5:
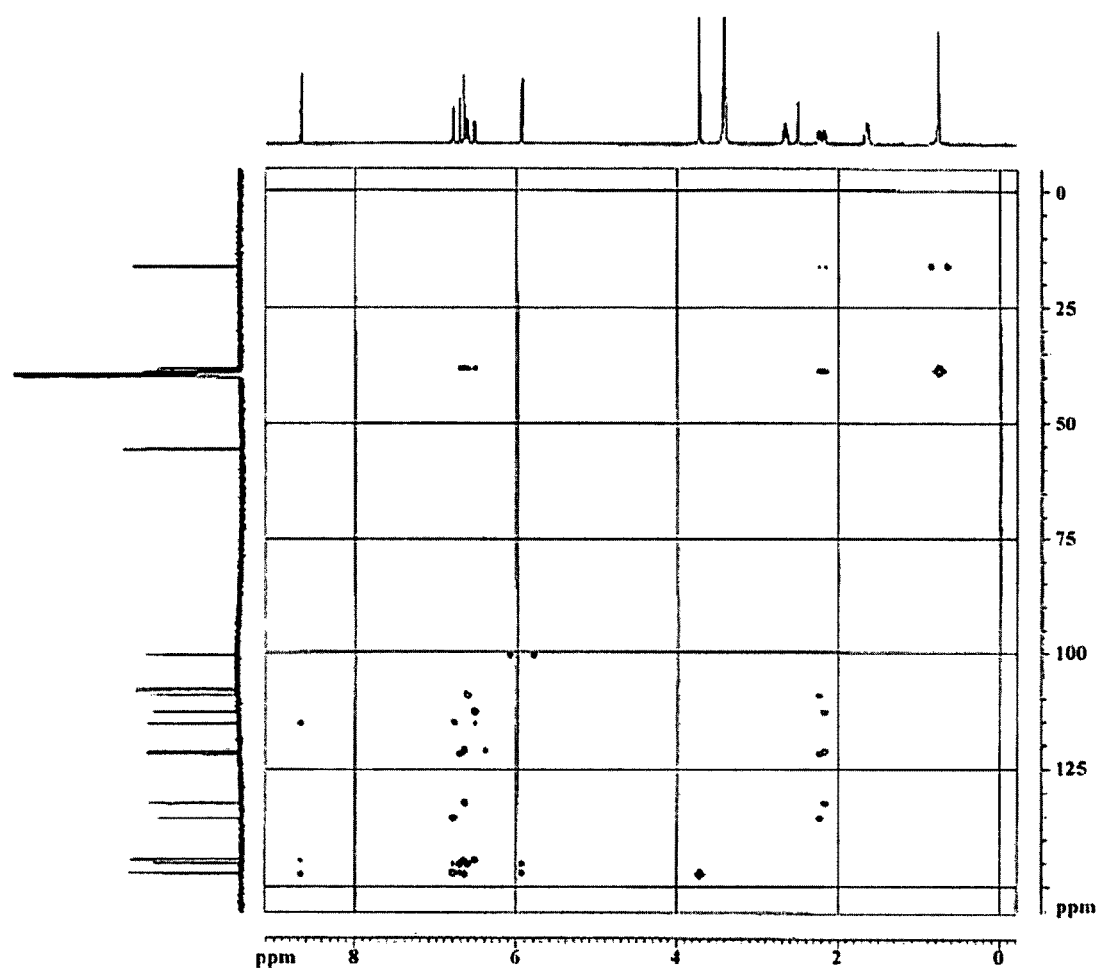
FIG. 5 is $^{1}H$-$^{13}C$ HMBC spectrum of macelignan according to the present invention.

To determine the structure of the single substance, fraction III-B-2, $^1$H-NMR spectrometry and $^{13}$C-NMR spectrometry were performed at 600 MHz and 150 MHz, respectively (solvent: DMSO). The results are shown in FIG. 2 and FIG. 3. To determine the $^1$H-$^1$H interrelation and $^1$H-$^{13}$C interrelation based on the results of $^1$H-NMR spectrometry and $^{13}$C-NMR spectrometry, $^1$H-$^1$H COSY spectrometry and $^1$H-$^{13}$C HMBC spectrometry were performed. The results are shown in FIG. 4 and FIG. 5. The following Table 1 shows the overall results of $^1$H-NMR, $^{13}$C-NMR, $^1$H-$^1$H COSY and $^1$H-$^{13}$C HMBC spectrometry.

TABLE 1

| Position | $^{13}$C-NMR | $^1$H-NMR | $^1$H-$^1$H COSY | $^1$H-$^{13}$C HMBC |
|---|---|---|---|---|
| 1 | 135.4 | | | |
| 2 | 109.2 | 6.72 brs | | C-7, C-6, C-4, C-3 |
| 3 | 147.3 | | | |
| 4 | 145.1 | | | |
| 5 | 107.9 | 6.79 d(7.8) | 6.61 | C-6, C-4, C-3, C-1 |
| 6 | 121.7 | 6.61 dd(7.8) | 6.79 | C-7, C-5, C-4, C-2, C-1 |
| 7 | 38.2 | 2.23 dd(13.2, 9.3) | 1.64, 2.66 | C-8, C-6, C-2, C-1 |
| | | 2.66 dd(13.2, 4.8) | 1.64, 2.23 | C-9, C-8, C-6, C-2, C-1 |
| 8 | 38.7 | 1.64 brs | 0.75, 2.23, 2.66 | C-7 |
| 9 | 16.0 | 0.75 d(6.3) | 1.64 | C-8, C-7 |
| 1' | 132.4 | | | |
| 2' | 112.9 | 6.66 brs | | C-7', C-6', C-4', C-3' |
| 3' | 147.1 | | | |
| 4' | 144.4 | | | |
| 5' | 115.2 | 6.66 d(7.9) | 6.53 | C-6', C-4', C-3', C-1' |
| 6' | 121.0 | 6.53 d(7.9, 1.1) | 6.66 | C-7', C-5', C-4', C-2', C-1' |
| 7' | 38.0 | 2.17 dd(13.2, 9.3) | 1.64, 2.66 | C-8', C-6', C-2', C-1' |
| | | 2.66 dd(13.2, 4.8) | 1.64, 2.17 | C-9', C-8', C-6', C-2', C-1' |
| 8' | 38.7 | 1.64 brs | 0.75, 2.17, 2.66 | C-7' |
| 9' | 16.1 | 0.75 d(6.3) | 1.64 | C-8', C-7' |
| OMe | 55.5 | 3.72 (s) | | |
| O-CH$_2$-O | 100.6 | 5.95 d(4.8) | | C-3, C-4 |

<1-3> Mass Spectrometry

Figure 6:
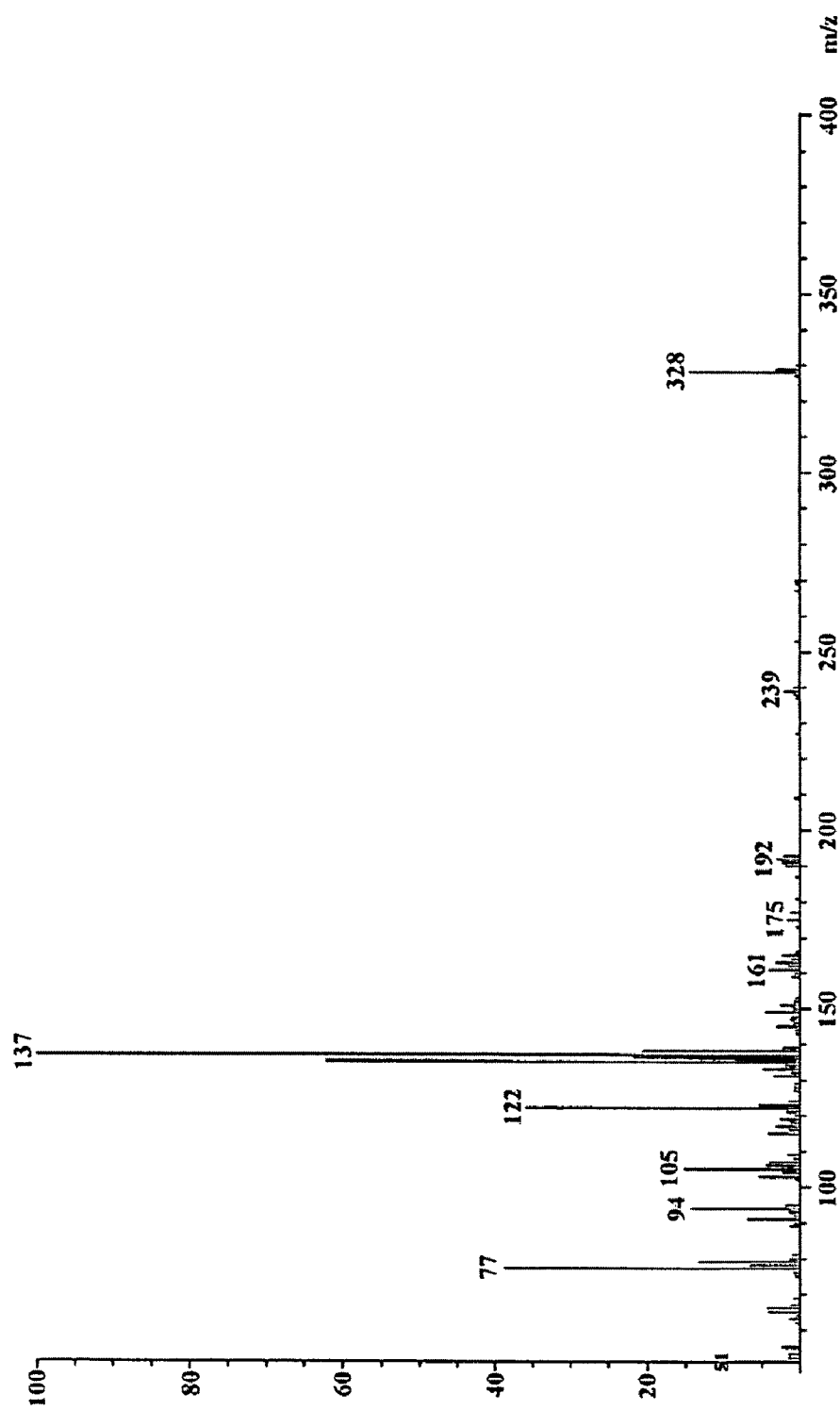
FIG. 6 is EI-Mass spectrum of macelignan according to the present invention.

EI/MS of the isolated single substance, III-B-2 was performed to determine the molecular weight. The results of mass spectrometry are shown in FIG. 6. It was shown that the compound had a molecular weight of 328 as determined by [M] of m/z 328, and was represented by a molecular formula of $C_{20}H_{24}O_4$.

<1-4> Measurement of Specific Rotation Value

First, 20 mg of the isolated single substance, III-B-2 were dissolved into 2 ml of chloroform (CHCl$_3$). Then, the specific rotation value ([α]$_D$) of the compound was measured by using a polarimeter (Automatic Polarimeter, APIII-89, Rodulph, N.J., USA). After the measurement, it was shown that [a]$_D$=+ 4.0 (CHCl$_3$, c=1.0).

After judging the above results of $^1$H-NMR, $^{13}$C-NMR, $^1$H-$^1$H COSY, $^1$H-$^{13}$C HMBC, EI/MS spectrometry and ([α]$_D$) compared to a known report (Woo, W. S. et al., *Phytochemistry*, 26: 1542-1543, 1987), it could be seen that the isolated single substance was macelignan represented by the following Formula I:

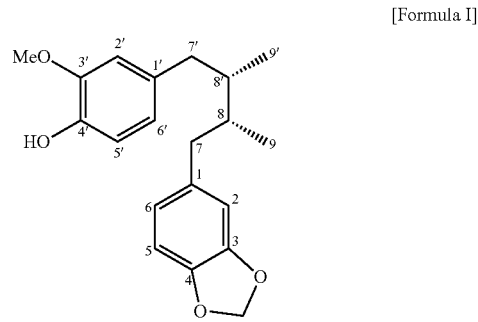

[Formula I]

Example 2

Activation of PPAR by Macelignan

<2-1> Activation of PPARα by Macelignan

To investigate whether macelignan acts as a ligand of PPAR or not, it was tested according to known method (*Cell*, 68: 879-887, 1992; *J. Biol. Chem.*, 272: 25252-25259, 1997) using a plasmid expressing PPAR and a vector having PPRE-controlled luciferase genes.

Activation of luciferase expression was measured by transfecting COS-7 monkey kidney cells (ATCC CRL-1651) with the PPARα plasmid and pFR-luciferase vector (Stratagene, USA), and then by treating the transfected cells with macelignan isolated from Example 1 for 24 hours. The PPARα plasmid was obtained by isolating polynucleotide encoding the amino acid sequence of amino acids 200~510 (i.e. PPARα ligand-bound domain of the total amino acid sequence of human PPARα (Genbank Acession No. S74349)) with the primers of SEQ ID NO: 1 (CTTGGATCCGAACATGA-CATA) and SEQ ID NO: 2 (TGGGGTACCTGGCTGAT) by RT-PCR. Then, the polynucleotide was cloned between the restriction enzyme sites of BamHI and KpnI of pFA vector (Stratagene, USA). Herein, mRNA used as the template in RT-PCR was obtained by separating the total RNA in cultured Hep G2 (ATCC HB-8065) human liver cells by using TRI-ZOL (Invitrogen, USA). RT-PCR was performed by synthesizing cDNA using reverse transcriptase at 42° C. for 60 minutes, and 30 cycles of 1 minute at 95° C., 30 seconds at 54° C. and 2 minutes at 72° C. using Taq polymerase. At this time, the test groups treated with different concentrations (1, 5, 10 and 25 µM) of macelignan according to the present invention were compared to the control treated with 0.01% DMSO, and to the groups treated with different concentrations (1, 5, 10 and 25 μM) of Wy-14643 (Sigma, USA), a compound known as a PPARα ligand.

Figure 7:
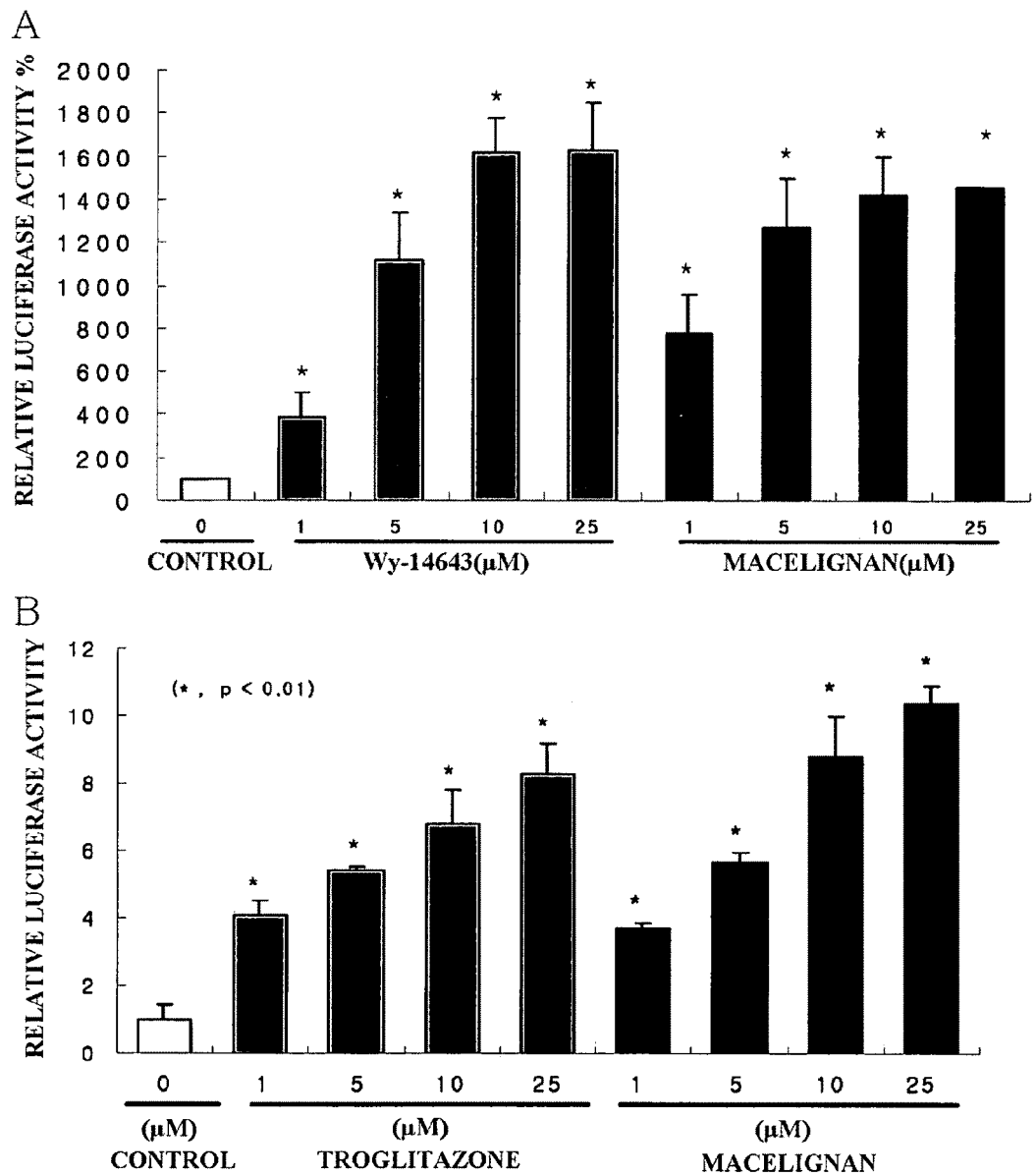
FIG. 7 is a graph illustrating the effect of macelignan according to the present invention upon the activation of PPARα (A) or PPARδ (B), in concentration.

As shown in FIG. 7A, macelignan increased PPARα activity in a concentration-dependent manner, and all the test groups treated with different concentrations of macelignan showed a significant difference (*, $p<0.01$) compared to the control. For example, when comparing both groups treated under a concentration of 25 μM to each other, the known compound Wy-14643 showed activity higher than the control by about 16 times, while the luciferase activity derived from the macelignan according to the present invention showed activity higher than the control by about 14 times. This indicates that the natural substance, macelignan, acts as a PPARα ligand to activate PPARα, and shows activity similar to that of Wy-14643, a known PPARα ligand, thereby activating PPARα effectively.

<2-2> Activation of PPARγ by Macelignan

To investigate whether macelignan activates PPARγ or not, it was tested according to the method of Example 2-1 except that PPARγ plasmid was used instead of PPARα plasmid and troglitazone was used instead of Wy-14643. Herein, the PPARγ plasmid was obtained by isolating polynucleotide encoding the amino acid sequence of amino acids 176-477 (i.e. PPARγ ligand-bound domain of the total amino acid sequence of human PPARγ (Genbank Acession No. NM_138712)) with the primers of SEQ ID NO: 3 (TCGGTT-TAAGATTCATCTTTATT) and SEQ ID NO: 4 (GTCTCCG-GTACCTTGATCACCTGC) by RT-PCR. Then, the polynucleotide was cloned between the restriction enzyme sites of XbaI and KpnI of pFA vector (Stratagene, USA).

As shown in FIG. 7B, macelignan increased PPARγ activity in a concentration-dependent manner, and all the test groups treated with different concentrations of macelignan showed a significant difference (*, $p<0.01$) when compared with the control. For example, when comparing both groups treated under a concentration of 25 μM to each other, the known compound troglitazone showed activity higher than the control by about 8.3 times, while the luciferase activity derived from the macelignan according to the present invention showed activity higher than the control by about 10.4 times. This indicates that macelignan acts as a PPARγ ligand to activate PPARγ, shows activity higher than that of troglitazone, a known drug compound, and thus is more efficient for the activation of PPAR γ receptors.

Example 3

Determination of Expression of Target Genes Induced by PPAR Activation of Macelignan <3-1> Determination of Expression of Target Genes of PPARα

SK-HEP-1 liver cells (ATCC CL-173) cultured in a DMEM medium containing 10% FBS were pipetted into a multi-well plate in a cell count of $1\times10^6$ cells per well, and then further cultured for 5 hours. Different concentrations (1, 5, 10 and 25 μM) of macelignan were added to the medium of the cultured cells, and then the cells were left for 24 hours. The cells were collected and the total RNA was isolated by using TRIZOL (Invitrogen, USA). The total RNA isolated as described above was determined and cDNA was synthesized by using reverse transcriptase at 42° C. for 20 minutes with same amounts of RNA. The cDNA was subjected to RT-PCR by repeating 30 cycles of 95° C./1 minute, 56° C./30 seconds and 72° C./2 minutes with the following primers and Taq polymerase: primers for CD36 amplification (SEQ ID NO: 5(CGGCGATGAGAAAGCAGAA) and SEQ ID NO: 6(CAACCAGGCCCAGGAGC)), primers for CPT-1 amplification (SEQ ID NO: 7(AGACGGTGGAACAGAGGCT-GAAG) and SEQ ID NO: 8(TGAGACCAAACAAAGT-GATGATGTCAG)), primers for PDK4 amplification (SEQ ID NO: 9(TCAAATCAAAATAGCCTTCCC) and SEQ ID NO: 10(ATAAGTTAAGTGGGCCTGG)), and primers for ACO amplification (SEQ ID NO: 11(GGGCATGGCTAT-TCTCATTGC) and SEQ ID NO: 12(CGAACAAGGTCAA-CAGAAGTTAGGTTC)).

Figure 8:
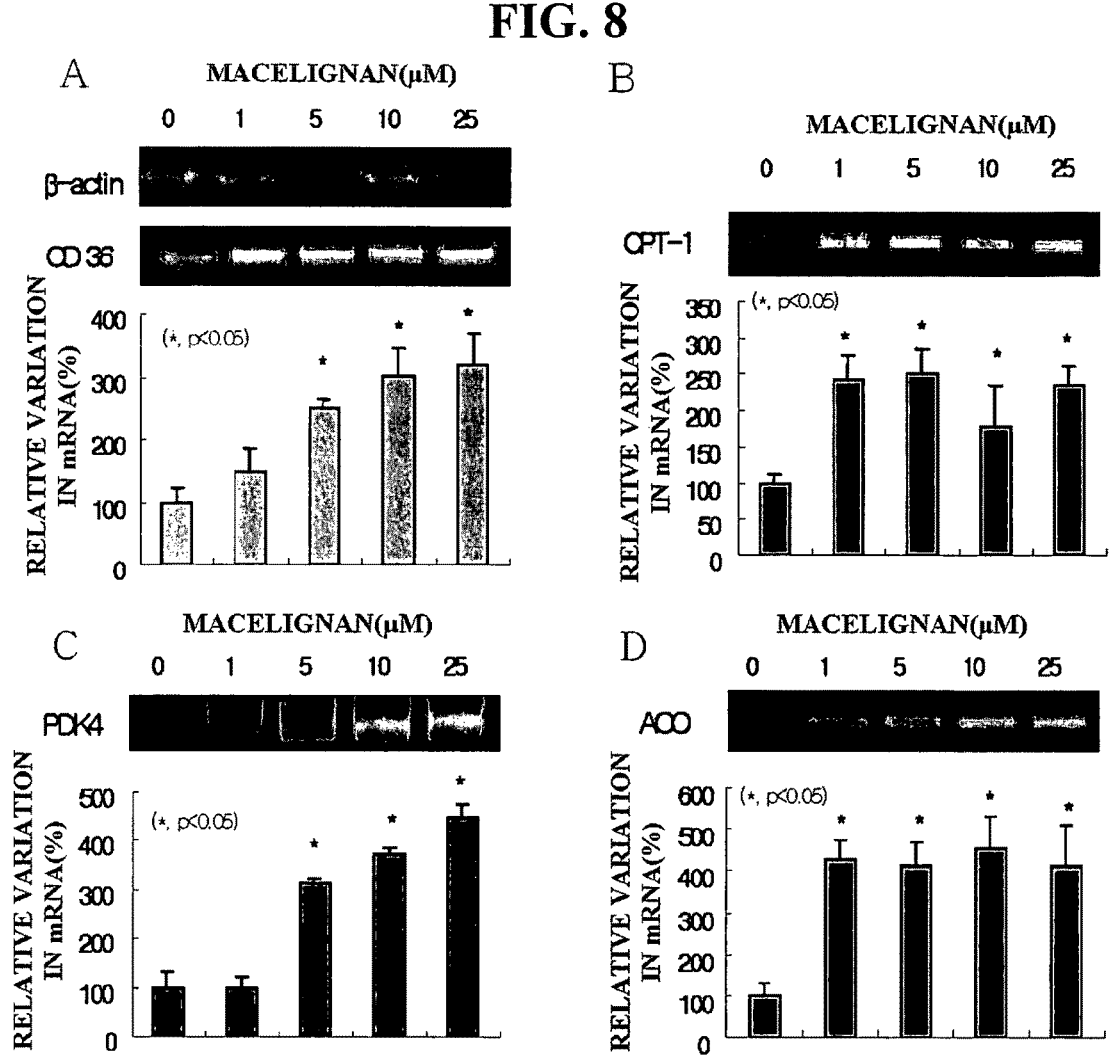
FIG. 8 is a result showing the effect of macelignan according to the present invention upon the expression of target genes of PPARα;
A: CD36
B: CPT-1
C: PDK4
D: ACO.

As shown in FIG. 8, mRNA expression of CD36, CPT-1, PDK-4 and ACO (target genes) whose expression is increased by PPARα, was significantly increased by the treatment with macelignan in all the test groups, when compared with the control (*, $p<0.01$; **, $p<0.05$). This indicates that macelignan can activate PPARα, and control the expression of target genes of PPARα.

<3-2> Determination of Expression of Target Genes of PPARα

3T3-L1 mouse pre-adipocytes (ATCC CL-173) cultured in a DMEM medium containing 10% FBS were pipetted into a multi-well plate in a cell count of $1\times10^6$ cells per well, and then further cultured for 5 hours. To the medium of the cultured cells, 10 μM of macelignan was added and then left for 24 hours. Adipocyte differentiation was induced by substituting the medium of the cultured cells with MDI (0.5 mM 3-isobutyl-1-methylxanthine, 0.5 uM dexamethasone, 10 ug/ml insulin) medium (*Am. J. Physiol. Cell Physiol.*, 280: C807-C813, 2001). Cells were collected two days after the substitution of MDI medium, and the total RNA was isolated by using TRIZOL (Invitrogen, USA). The total RNA isolated as described above was determined, and cDNA was synthesized by using reverse transcriptase at 42° C. for 20 minutes with same amount of RNA. The cDNA was subjected to RT-PCR by repeating 30 cycles of 95° C./1 minute, 56° C./30 seconds and 72° C./2 minutes with the following primers and Taq polymerase: primers for LPL amplification (SEQ ID NO: 13(TATCCGCGTGATTGCAGAGA) and SEQ ID NO: 14(AGAGAGTCGATGAAGAGATGAATGG)), and primers for PEPCK amplification (SEQ ID NO: 15(CAGGCG-GCTGAA GAAGTATGA) and SEQ ID NO: 16(AAC-CGTCTTGCTTTCGATCCT)).

Figure 9:
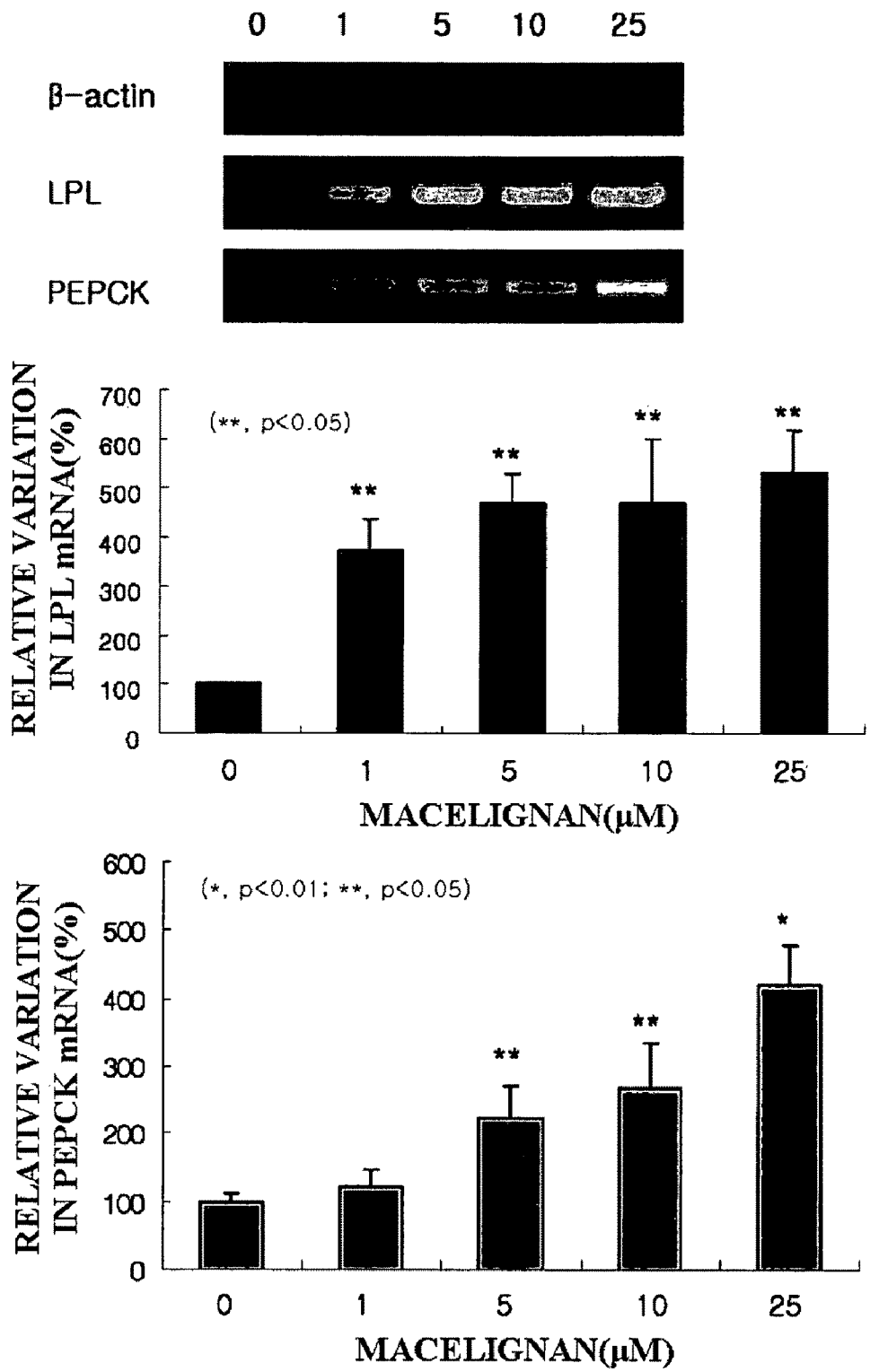
FIG. 9 is a result showing the effect of macelignan according to the present invention upon the expression of target genes of PPARγ;
A: LPL
B: PEPCK

As shown in FIG. 9, mRNA expression of LPL and PEPCK (target genes), whose expression is increased by PPARγ, was significantly increased by the treatment with macelignan in all the test groups in proportion to the macelignan concentration, when compared with the control (*, $p<0.01$; **, $p<0.05$). This indicates that macelignan can activate PPARγ, and control the expression of target genes of PPARγ.

Example 4

Determination of Stimulation of Adipocyte Differentiation Induced by PPAR Activation of Macelignan 3T3-L1 mouse pre-adipocytes cultured in a DMEM medium containing 10% FBS were pipetted into a multi-well plate in a cell count of $1\times10^6$ cells per well, and then further cultured for 5 hours. To the cultured cells, 10 μM of macelignan was added and then left for 24 hours. Adipocyte differentiation was induced by substituting the medium of the cultured cells with MDI (0.5 mM 3-isobutyl-1-methylxanthine, 0.5 uM dexamethasone, 10 ug/ml insulin) medium (*Am. J. Physiol. Cell Physiol.*, 280: C807-C813, 2001). The shape of the cells was observed by an optical microscope two day after the substitution of MDI medium.

Figure 10:
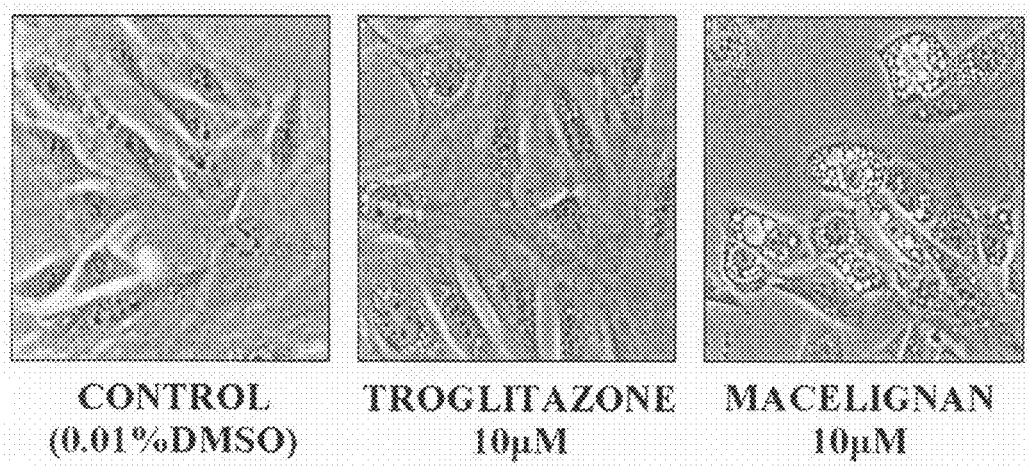
FIG. 10 is a result showing the effect of macelignan according to the present invention upon the differentiation of adipocytes 3T3-L1 of mouse fibroblasts.

As shown in FIG. 10, adipocyte differentiation was stimulated in the group treated with macelignan (10 μM) when compared with the control treated with 0.01% DMSO instead of macelignan and to the group treated with 10 μM of troglitazone. This indicates that macelignan can activate PPAR to maximize sugar absorption of adipocytes and to stimulate adipocyte differentiation.

Example 5

Investigation of Anti-Diabetes Effect of Macelignan in Obesity/Diabetes Mouse Model A mouse (db/db mouse; The Jackson Laboratory, USA) used in the present invention as an obesity/diabetes model is deficient in leptin genes and cannot control its appetite, and thus takes an excessive amount of food continuously. As a result, the mouse accumulates excessive fat in the body and shows overweight and hyperlipidemia when compared to a normal mouse. Thus, it can be a typical model of obesity and metabolic diseases. Additionally, it has a higher blood sugar level and can be a typical model of non-insulin-dependent diabetes mellitus.

To investigate the effect of preventing and treating diabetes of macelignan, seven mice of 10 week-aged obesity/diabetes mice (db/db mice) were used per test group. To the test groups, macelignan suspended in 0.25% carboxymethyl cellulose was orally administered with the dose of 5 mg/kg (body weight), 10 mg/kg (body weight) and 25 mg/kg (body weight), once per day at a predetermined time, for 14 days. As a control, 0.25% carboxymethyl cellulose was orally administered alone to normal mice in the same dose as administered to the test group. As another control, 0.25% carboxymethyl cellulose was orally administered alone to obesity/diabetes mice in the same dose as administered to the test group. As still another control, 10 mg/kg (body weight) of troglitazone was orally administered. Blood sugar levels of the obesity/diabetes mice were determined from six days before the administration, once per three days. On the $12^{th}$ day after the oral administration, the test group and the controls were subjected to the Oral Glucose Tolerance Test (OGTT). For this test, obesity/diabetes mice in the test group and the controls were fasted for at least 18 hours, glucose was orally administered to the mice in a dose of 3 g/kg (body weight), and then variations in the blood sugar were measured at 0 minutes, 30 minutes, 60 minutes and 120 minutes after the glucose administration. Additionally, on the $14^{th}$ day of the oral administration, the final blood sugar level, insulin content in blood (mouse insulin ELISA Kit, Linco Research, o. EZRMI-BK, USA) and adiponectin content in blood (Adiponectin Quantikine ELISA Kit, R&D systems, No. MRP300, USA) were analyzed.

Figure 11:
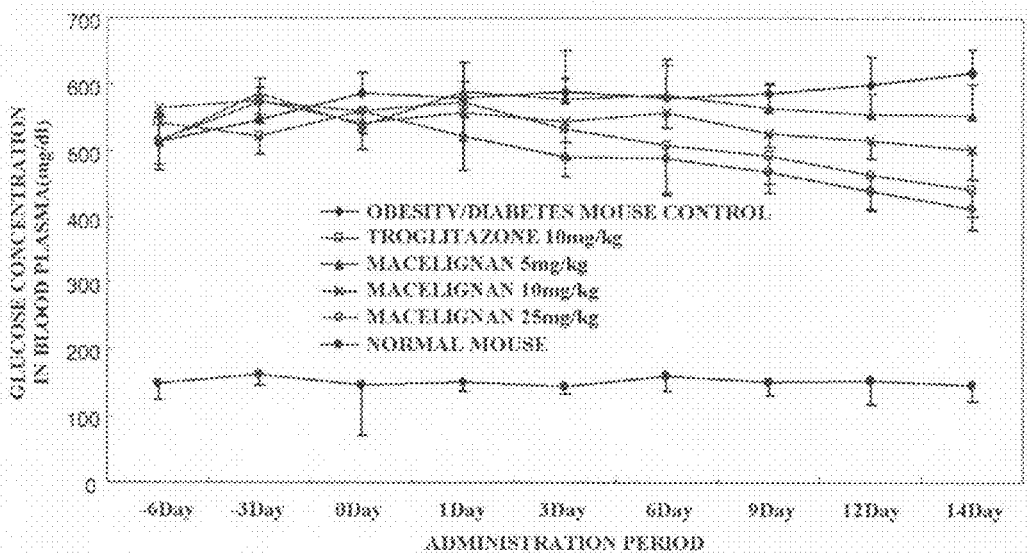
FIG. 11 is a result showing the effect of macelignan according to the present invention upon the blood sugar in an obesity/diabetes mouse model.

As a result of measuring the variations in blood sugar for 14 days from the administration day in the test group and in the controls, as shown in FIG. 11, the blood sugar level in the test group showed a tendency to decrease when compared to the controls. Particularly, 14 days after the oral administration, the blood sugar level in the obesity/diabetes mouse control was 618.61±35.03 mg/dl, while the test groups treated with macelignan in a dose of 5 mg/kg (body weight), 10 mg/kg (body weight) and 25 mg/kg (body weight) showed a drop in the blood sugar level to 552.84±47.95 mg/dl, 501.03±43.67 mg/dl and 412.74±31.15 mg/dl, respectively (p<0.05).

Figure 12:
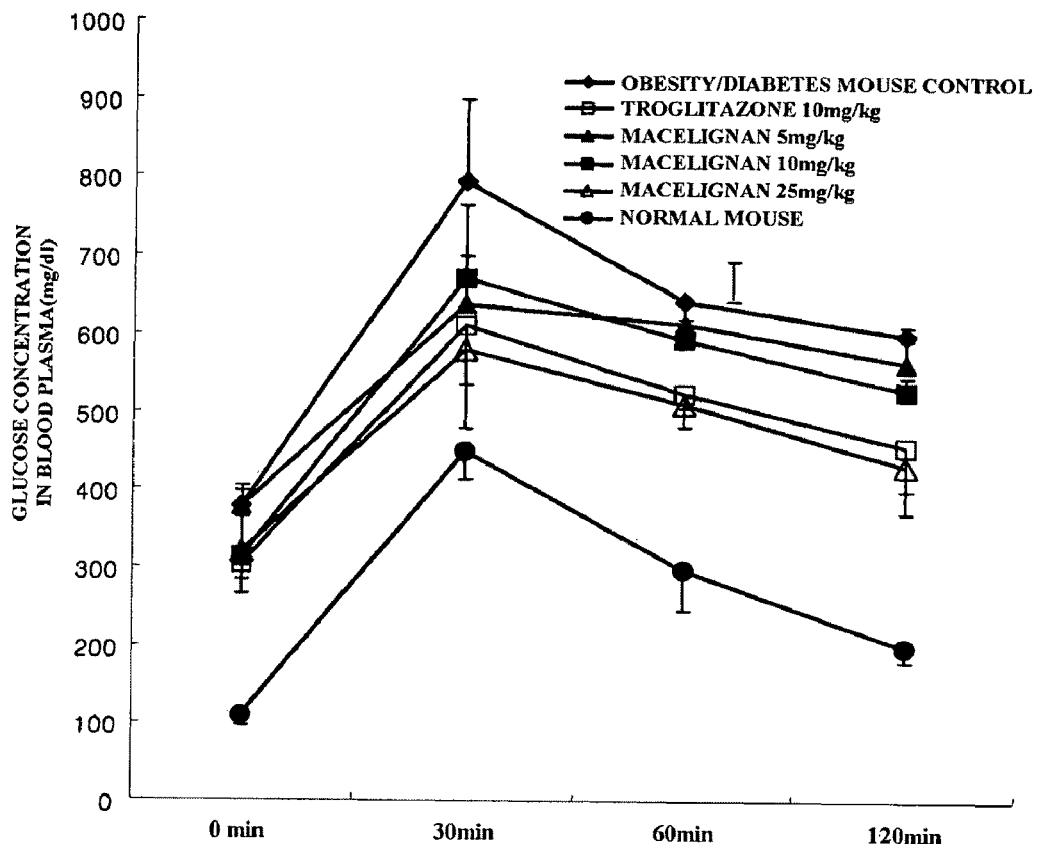
FIG. 12 is a graph illustrating the effect of macelignan according to the present invention upon the glucose tolerance in an obesity/diabetes mouse model.
Figure 13:
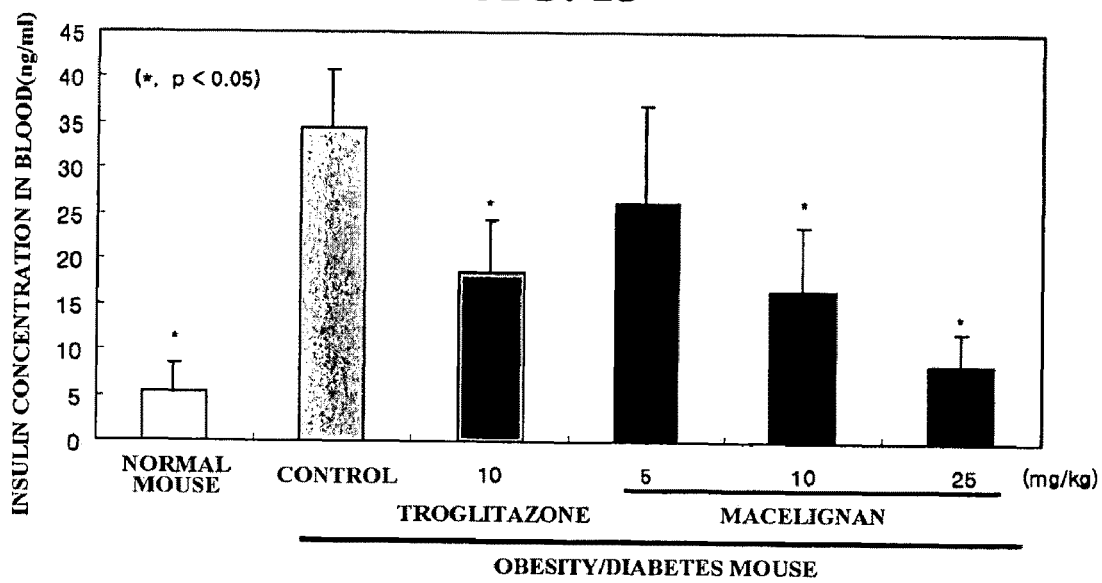
FIG. 13 is a graph illustrating the effect of macelignan according to the present invention upon the insulin concentration in blood in an obesity/diabetes mouse model.
Figure 14:
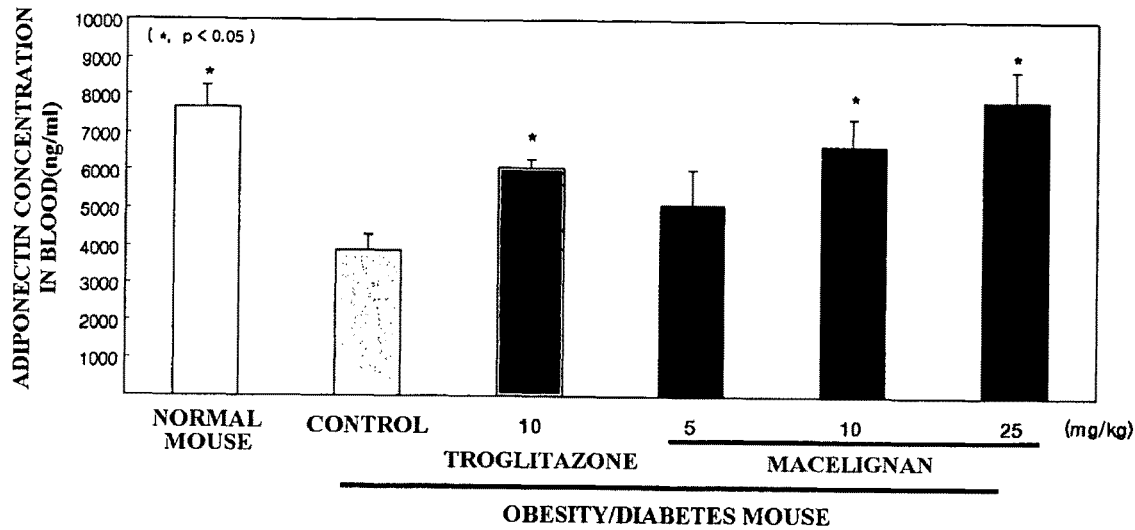
FIG. 14 is a graph illustrating the effect of macelignan according to the present invention upon the adiponectin concentration in blood in an obesity/diabetes mouse model.

Further, as results of carrying out OGGT and measuring insulin content in blood and adiponectin in blood, as shown in the following Table 2 and FIGS. 12~14, the test groups treated with macelignan showed a significant increase in glucose tolerance, a significant decrease in insulin concentration in blood, and a significant increase in adiponectin concentration in blood.

TABLE 2

| | | Normal mice | Negative Control | Triglitazone 10 mg/kg (body weight) | Macelignan 5 mg/kg (body weight) | Macelignan 10 mg/kg (body weight) | Macelignan 25 mg/kg (body weight) |
|---|---|---|---|---|---|---|---|
| OGTT (mg/dl) | 0 min. | 110.57 ± 13.70 | 378.14 ± 19.56 | 303.43 ± 37.83 | 379.14 ± 26.23 | 313.86 ± 51.40 | 319.14 ± 35.25 |
| | 30 mins. | 450.00 ± 35.49 | 795.14 ± 103.08 | 610.57 ± 76.21 | 636.85 ± 63.29 | 670.14 ± 94.20 | 580.00 ± 101.37 |
| | 60 mins. | 296.85 ± 51.21 | 643.01 ± 45.75 | 523.70 ± 17.10 | 613.38 ± 24.36 | 593.11 ± 27.15 | 509.70 ± 27.71 |
| | 120 mins. | 199.04 ± 17.77 | 600.35 ± 11.48 | 456.41 ± 54.69 | 564.21 ± 29.86 | 529.46 ± 17.55 | 431.21 ± 59.18 |
| Insulin concentration in blood (ng/ml) | | 5.25 ± 3.27 | 34.45 ± 6.33 | 18.57 ± 5.88 | 26.33 ± 10.78 | 16.66 ± 7.03 | 8.51 ± 3.67 |
| Adiponectin concentration in blood (ng/ml) | | 7666.86 ± 570.63 | 3881.14 ± 396.51 | 6682.33 ± 250.05 | 5111.14 ± 925.88 | 6882.86 ± 250.05 | 7864.00 ± 808.21 |

As can be seen from the overall results as described hereinabove, macelignan treatment in an obesity/diabetes mouse model can decrease insulin content in blood, increase adiponectin in blood, improve glucose tolerance and decrease blood sugar, so that macelignan is effective for improving insulin resistance and for preventing and treating diabetes mellitus.

Example 6

Evaluation of Anti-Obesity Effect of Macelignan

To investigate the anti-obesity effect of macelignan, seven mice of 10 week-aged obesity/diabetes mice (db/db mice) were used per test group. To the test groups, macelignan suspended in 025% carboxymethyl cellulose was orally administered in an administration dose of 5 mg/kg (body weight), 10 mg/kg (body weight) and 25 mg/kg (body weight), once per day at a predetermined time, for 14 days. As a control, 0.25% carboxymethyl cellulose was orally administered alone to normal mice in the same dose as administered to the test group. As another control, 0.25% carboxymethyl cellulose was orally administered alone to obesity/diabetes mice in the same dose as administered to the test group. As still another control, 10 mg/kg (body weight) of troglitazone was orally administered. From 6 days before the administration, diet intake and body weight of each obesity/diabetes mouse were measured once per three days. Additionally, on the $14^{th}$ day after the oral administration, white adipose tissue weight and the amount of triglyceride accumulated in muscle cell were measured (Triglyceride measuring kit, Wako, No. 432-40201, Japan).

Figure 15:
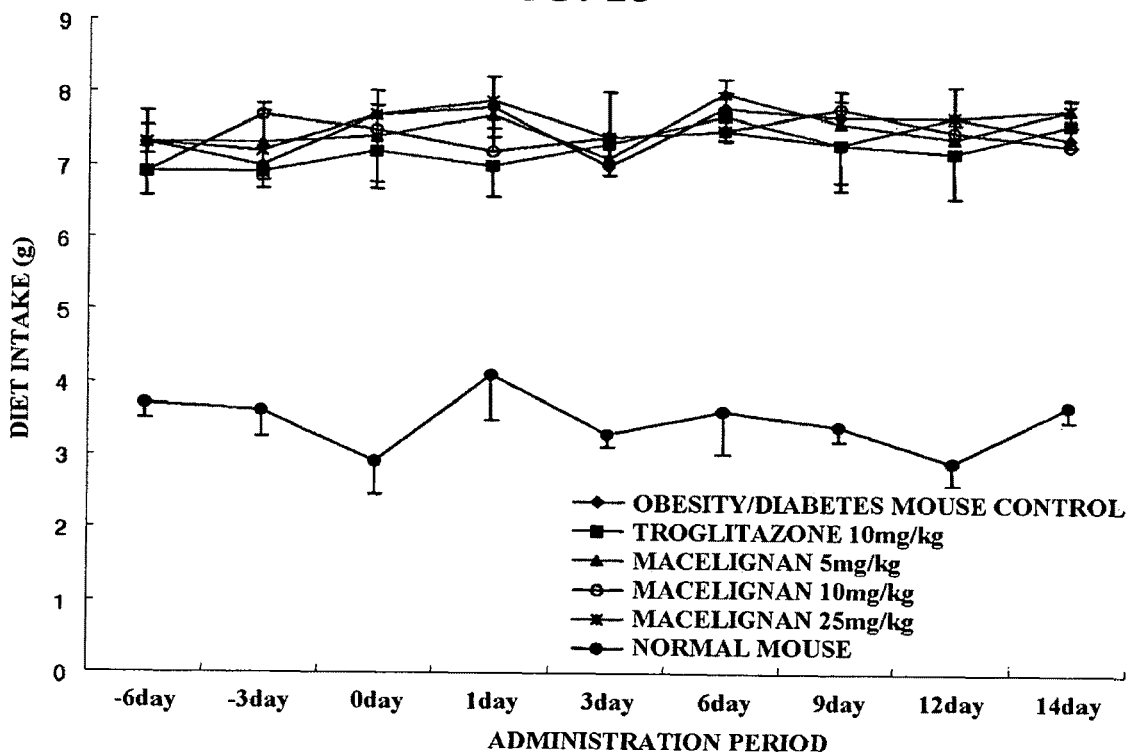
FIG. 15 is a graph illustrating the effect of macelignan according to the present invention upon the diet intake in an obesity/diabetes mouse model.
Figure 16:
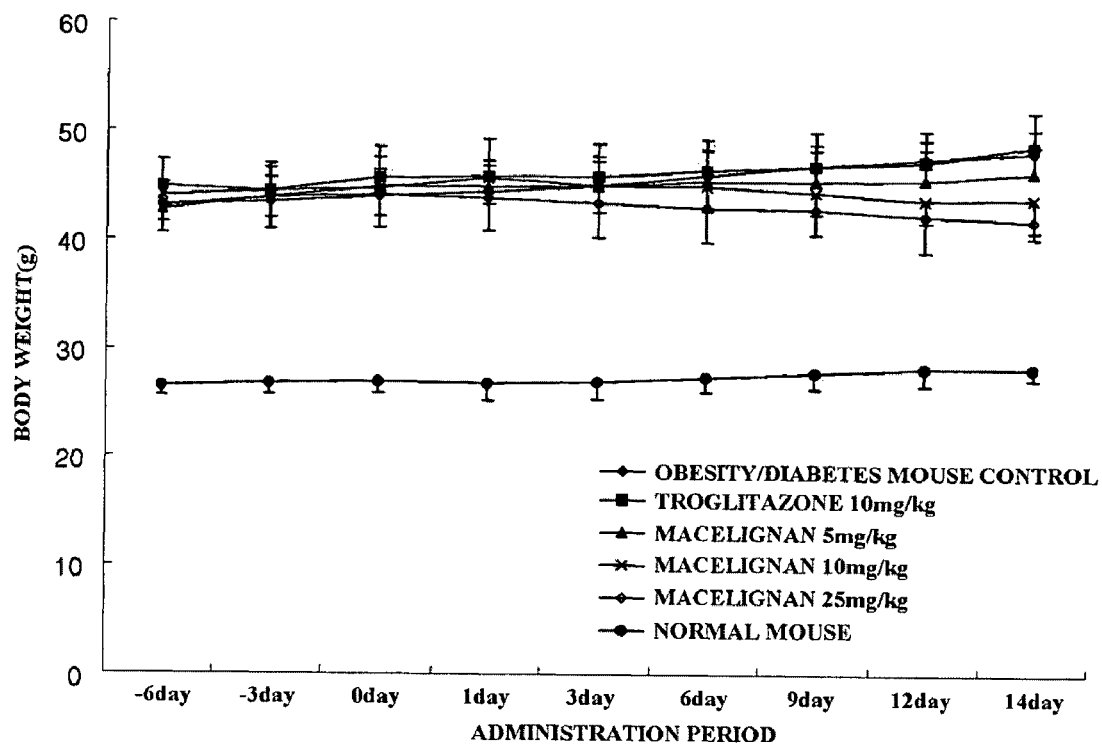
FIG. 16 is a graph illustrating the effect of macelignan according to the present invention upon the body weight in an obesity/diabetes mouse model.
Figure 17:
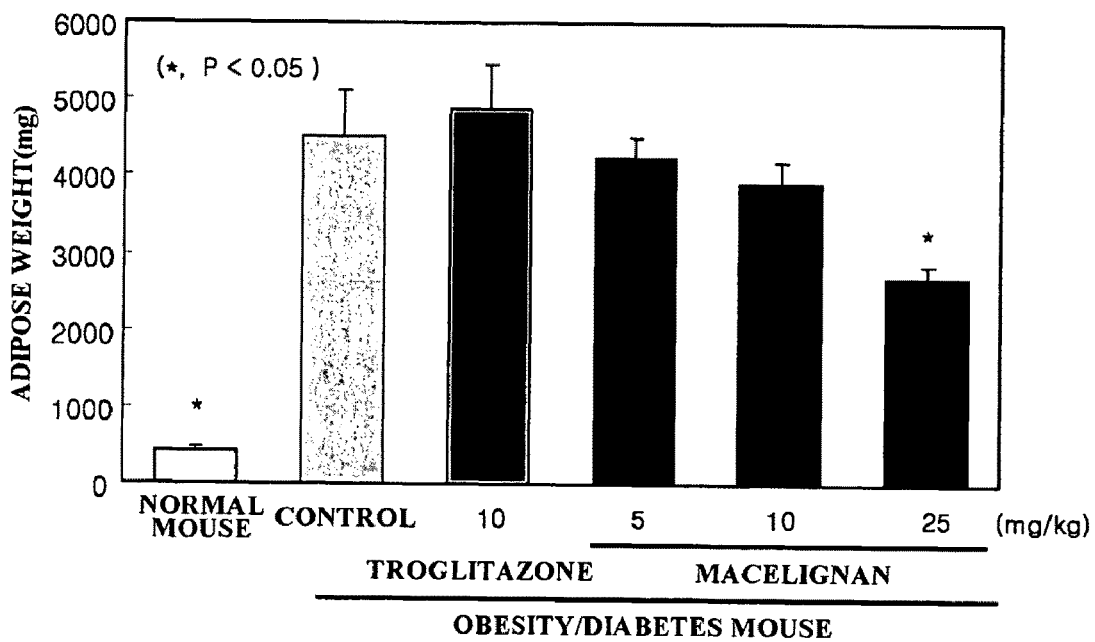
FIG. 17 is a graph illustrating the effect of macelignan according to the present invention upon the amount of adipose tissue in an obesity/diabetes mouse model.
Figure 18:
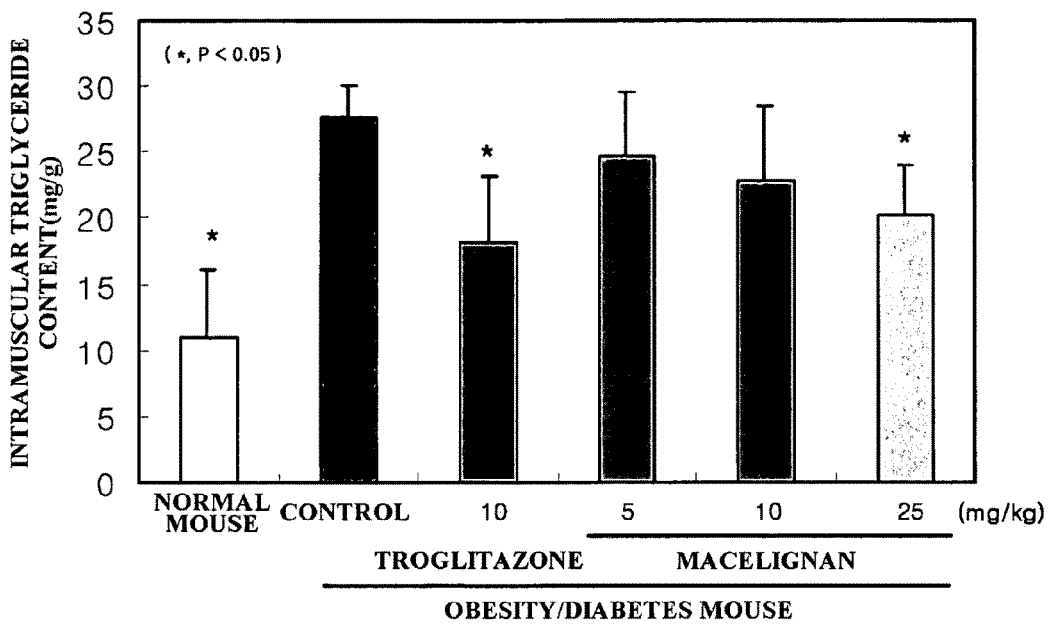
FIG. 18 is a graph illustrating the effect of macelignan according to the present invention upon the triglyceride concentration in muscle cell in an obesity/diabetes mouse model.
Figure 19:
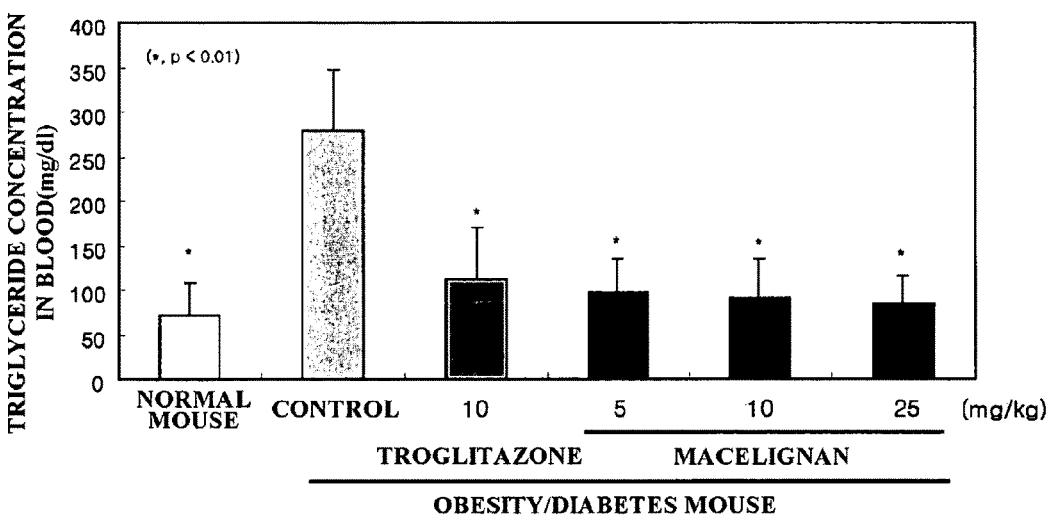
FIG. 19 is a graph illustrating the effect of macelignan according to the present invention upon the concentration of triglycerides in blood in an obesity/diabetes mouse model.
Figure 20:
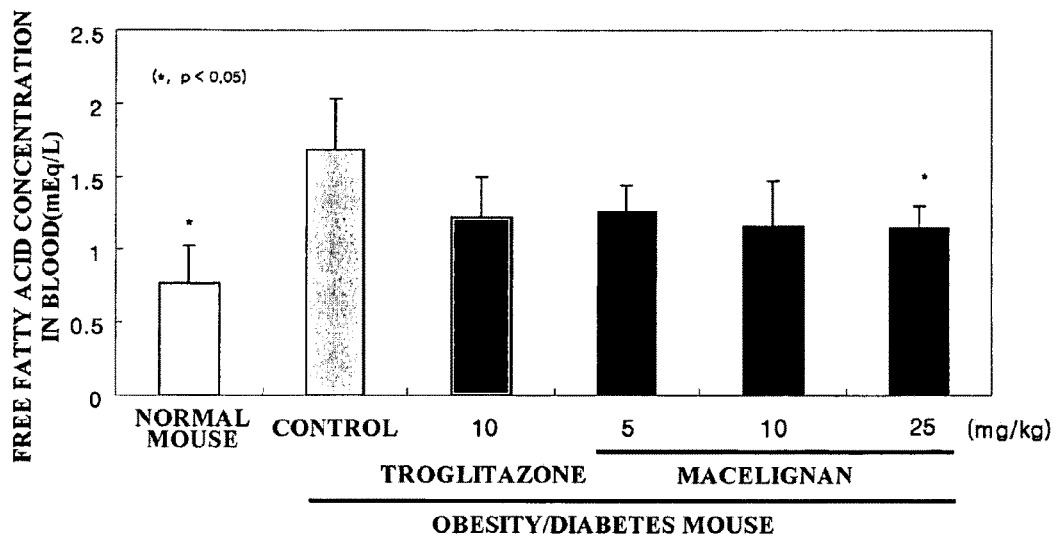
FIG. 20 is a graph illustrating the effect of macelignan according to the present invention upon the concentration of free fatty acids in blood in an obesity/diabetes mouse model.
Figure 21:
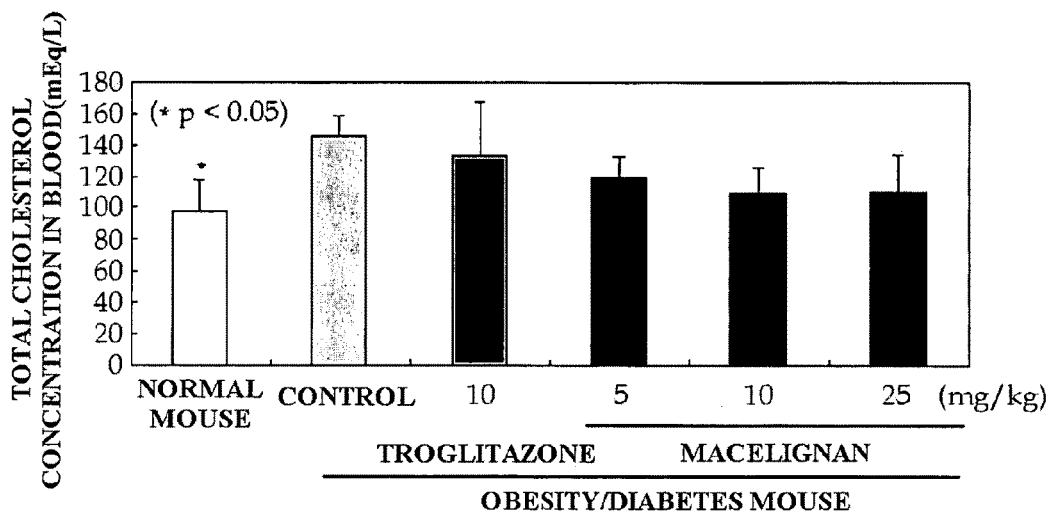
FIG. 21 is a graph illustrating the effect of macelignan according to the present invention upon the total cholesterol concentration in blood in an obesity/diabetes mouse model.
Figure 22:
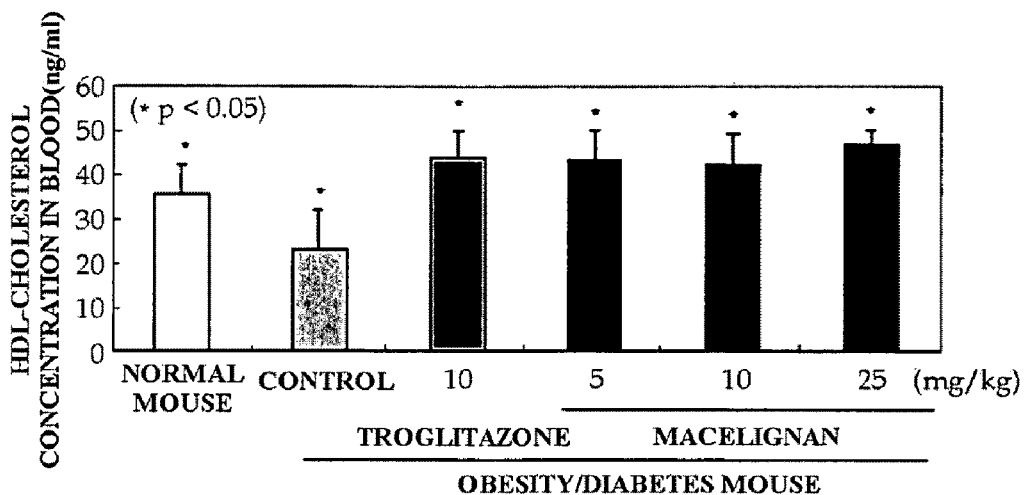
FIG. 22 is a graph illustrating the effect of macelignan according to the present invention upon the HDL-cholesterol concentration in blood in an obesity/diabetes mouse model.
Figure 23:
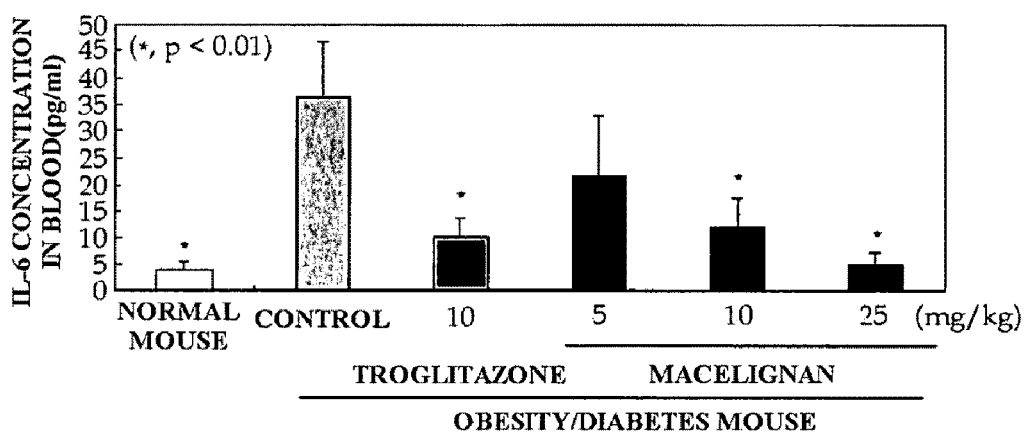
FIG. 23 is a graph illustrating the effect of macelignan according to the present invention upon the IL-6 concentration in blood in an obesity/diabetes mouse model.
Figure 24:
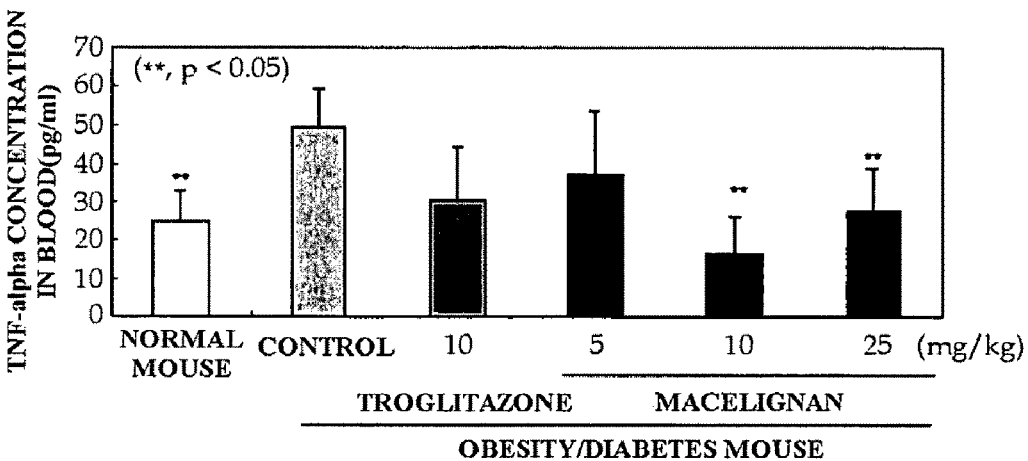
FIG. 24 is a graph illustrating the effect of macelignan according to the present invention upon the TNF-α, concentration in blood in an obesity/diabetes mouse model.

As a result of measuring the variations in diet intake and body weight in the test group and in the controls for 14 days after the administration, as shown in FIG. 15, the test groups and the controls had no significant difference in terms of diet intake. On the contrary, as shown in FIG. 16, when measuring on the 14$^{th}$ day of the oral administration, mice in the control showed a body weight of 48.16±2.09 g, while the test groups treated with macelignan in a dose of 5 mg/kg (body weight), 10 mg/kg (body weight) and 25 mg/kg (body weight) showed a drop in body weight to 46.32±2.31 g, 43.8±2.94 g and 41.80±1.56 g, respectively (p<0.05). Additionally, on the 14$^{th}$ day after the oral administration, as shown in FIG. 17, the control showed a white adipose tissue weight of 4508.30±605.20 mg, while the test groups treated with macelignan in a dose of 5 mg/kg (body weight), 10 mg/kg (body weight) and 25 mg/kg (body weight) showed a drop in a white adipose tissue weight to 4231.9±284.5 g, 3904.1±278.6 g and 2689.40±154.2 g, respectively (p<0.05). Further, as shown in FIG. 18, the control showed an intramuscular triglyceride accumulation of 27.62±2.44 mg, while the test groups treated with macelignan in a dose of 5 mg/kg (body weight), 10 mg/kg (body weight) and 25 mg/kg (body weight) showed a drop in intramuscular triglyceride accumulation to 24.73±4.74 g, 22.80±5.76 g and 20.24±3.82 g, respectively (p<0.05). As can be seen from the above results, in an obesity/diabetes model, oral administration of macelignan can decrease the body weight, adipose tissue weight and intramuscular fat accumulation. Therefore, macelignan is effective for preventing and treating obesity.

Example 7

Investigation of Effect of Macelignan upon Hyperlipidemia and Cardiovascular Diseases To investigate effects of macelignan upon the treatment of hyperlipidemia and cardiovascular diseases, seven mice of 10 week-aged obesity/diabetes mice (db/db mice) were used per test group. To the test groups, macelignan suspended in 0.25% carboxymethyl cellulose was orally administered in an administration dose of 5 mg/kg (body weight), 10 mg/kg (body weight) and 25 mg/kg (body weight), once per day at a predetermined time, for 14 days. As a control, 0.25% carboxymethyl cellulose was orally administered alone to normal mice in the same dose as administered to the test group. As another control, 0.25% carboxymethyl cellulose was orally administered alone to obesity/diabetes mice in the same dose as administered to the test group. As still another control, 10 mg/kg (body weight) of troglitazone was orally administered.

Fourteen days after the administration, triglyceride concentration in blood (triglyceride measuring kit, Wako, Japan), free fatty acid concentration in blood (free fatty acid measuring kit, Wako, Japan), total cholesterol content in blood (ASAN T-CHO-Lq Reagents, Asan Pharmaceutical Co. Ltd., Korea), HDL-cholesterol content in blood (ASAN HDL-Cholesterol, Asan Pharmaceutical Co. Ltd., Korea), IL-6 content in blood (IL-6 Quantikine ELISA, R&D systems, USA) and TNF-α content in blood were measured for the test groups and the controls.

As shown in the following Table 3 and FIGS. 19~24, triglyceride concentration, free fatty acid concentration, IL-6 content and TNF-α content in blood significantly decreased. There was no significant difference in total cholesterol content in blood between the control and the test groups. However, HDL-cholesterol content in blood significantly increased in the test groups.

TABLE 3

|  | Normal mice | Negative control | Triglitazone 10 mg/kg (body weight) | Macelignan 5 mg/kg (body weight) | Macelignan 10 mg/kg (body weight) | Macelignan 25 mg/kg (body weight) |
|---|---|---|---|---|---|---|
| Triglyceride in blood (mg/dl) | 72.57 ± 36.36 | 279.29 ± 67.89 | 112.57 ± 57.47 | 98.71 ± 36.62 | 91.71 ± 44.04 | 84.00 ± 31.24 |
| Free fatty acid in blood (mEq/l) | 0.76 ± 0.27 | 1.69 ± 0.34 | 1.22 ± 0.27 | 1.26 ± 0.19 | 1.16 ± 0.31 | 1.14 ± 0.15 |
| Total cholesterol in blood (ng/ml) | 98.33 ± 19.69 | 146.29 ± 12.67 | 133.67 ± 34.86 | 118.86 ± 13.75 | 109.71 ± 15.25 | 110.40 ± 23.72 |
| HDL-cholesterol in blood (ng/ml) | 35.74 ± 6.41 | 23.07 ± 8.97 | 43.85 ± 6.34 | 43.50 ± 6.73 | 42.17 ± 7.29 | 46.58 ± 3.89 |
| IL-6 in blood (pg/ml) | 3.97 ± 1.60 | 36.42 ± 10.2 | 10.24 ± 3.60 | 21.42 ± 11.42 | 12.04 ± 5.47 | 4.86 ± 2.46 |
| TNF-α in blood (pg/ml) | 24.99 ± 8.04 | 49.59 ± 9.86 | 30.49 ± 13.18 | 36.92 ± 16.27 | 16.41 ± 9.60 | 27.54 ± 9.77 |

Therefore, it can be seen from the above results that macelignan is effective for preventing and treating hyperlipidemia and cardiovascular diseases, because the test groups treated with macelignan in the obesity/diabetes mouse model show a drop in the concentration of triglycerides, concentration of free fatty acids, IL-6 concentration and TNF-α concentration in blood, and an increase in HDL-cholesterol content.

Example 8

Investigation of Effect of Macelignan upon Prevention and Treatment of Fatty liver To investigate effects of macelignan upon the prevention and treatment of fatty liver, seven mice of 10 week-aged obesity/diabetes mice (db/db mice) were used per test group. To the test groups, macelignan suspended in 0.25% carboxymethyl cellulose was orally administered in an administration dose of 5 mg/kg (body weight), 10 mg/kg (body weight) and 25 mg/kg (body weight), once per day at a predetermined time, for 14 days in all. As a control, 0.25% carboxymethyl cellulose was orally administered alone to normal mice in the same dose as administered to the test group. As another control, 0.25% carboxymethyl cellulose was orally administered alone to obesity/diabetes mice in the same dose as administered to the test group. As still another control, 10 mg/kg (body weight) of troglitazone was orally administered. Fourteen days after the oral administration, the liver tissue was isolated and crushed to extract the total lipid and fat contents, and then the triglyceride content accumulated in the liver tissue was measured.

Figure 25:
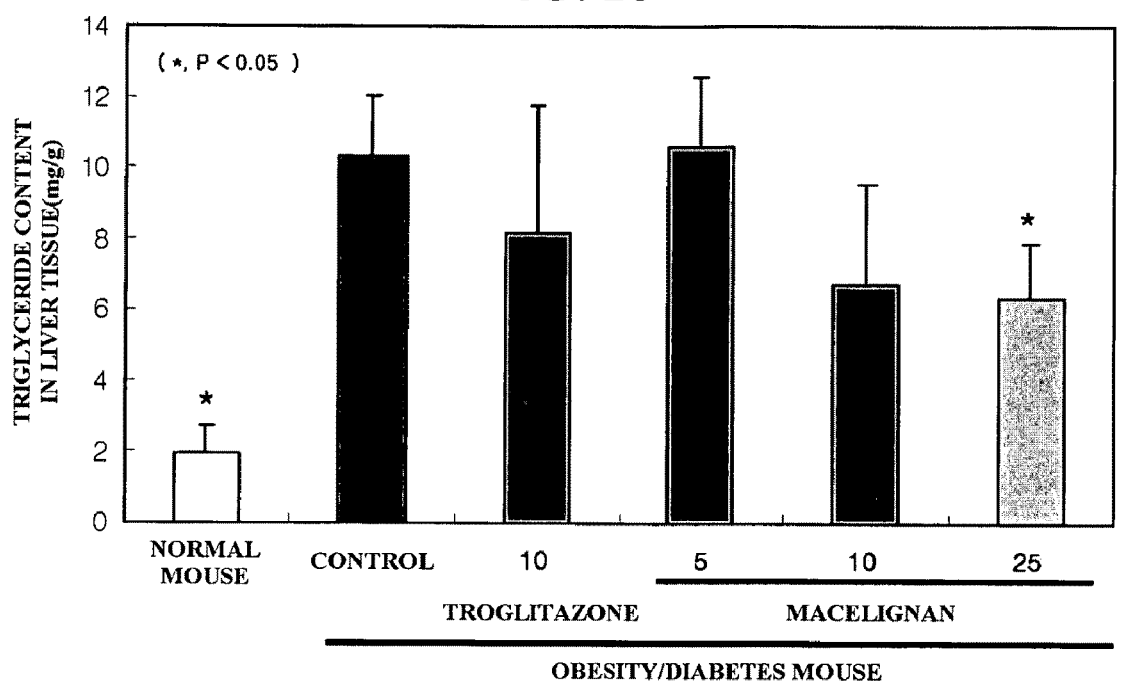
FIG. 25 is a graph illustrating the effect of macelignan according to the present invention upon the amount of triglycerides in the liver tissue in an obesity/diabetes mouse model.

As shown in FIG. 25, the triglyceride content in the liver tissue was 10.32±1.72 mg/g in the control, while the triglyceride content in blood, which was 6.30±11.59 mg/g, was significantly decreased in the test group treated with 25 mg/kg of macelignan (*, $p<0.05$). Therefore, it can be seen that macelignan is effective for preventing and treating fatty liver.

Example 9

Determination of Expression of Target Genes Induced by PPAR Activation in Obesity/Diabetes Mouse Model <9-1> Determination of Expression of Target Genes of PPARα

Liver tissue was removed from the test groups and the controls treated by oral administration in Examples 5~8. The liver tissue was homogenized in liquid nitrogen and the total RNA was isolated from the tissues by using TRIZOL (Invitrogen, USA). The total RNA isolated as described above was determined and cDNA was synthesized by using reverse transcriptase at 42° C. for 20 minutes with same amount of RNA. The cDNA was subjected to RT-PCR by repeating 30 cycles of 95° C./1 minute, 56° C./30 seconds and 72° C./2 minutes with the following primers and Taq polymerase: primers for CD36 amplification (SEQ ID NO: 5 and SEQ ID NO: 6), primers for ACO amplification (SEQ ID NO: 11 and SEQ ID NO: 12), and primers for CPT-1 amplification (SEQ ID NO: 7 and SEQ ID NO: 8). Expression of the genes was determined by real-time PCR.

Figure 26:
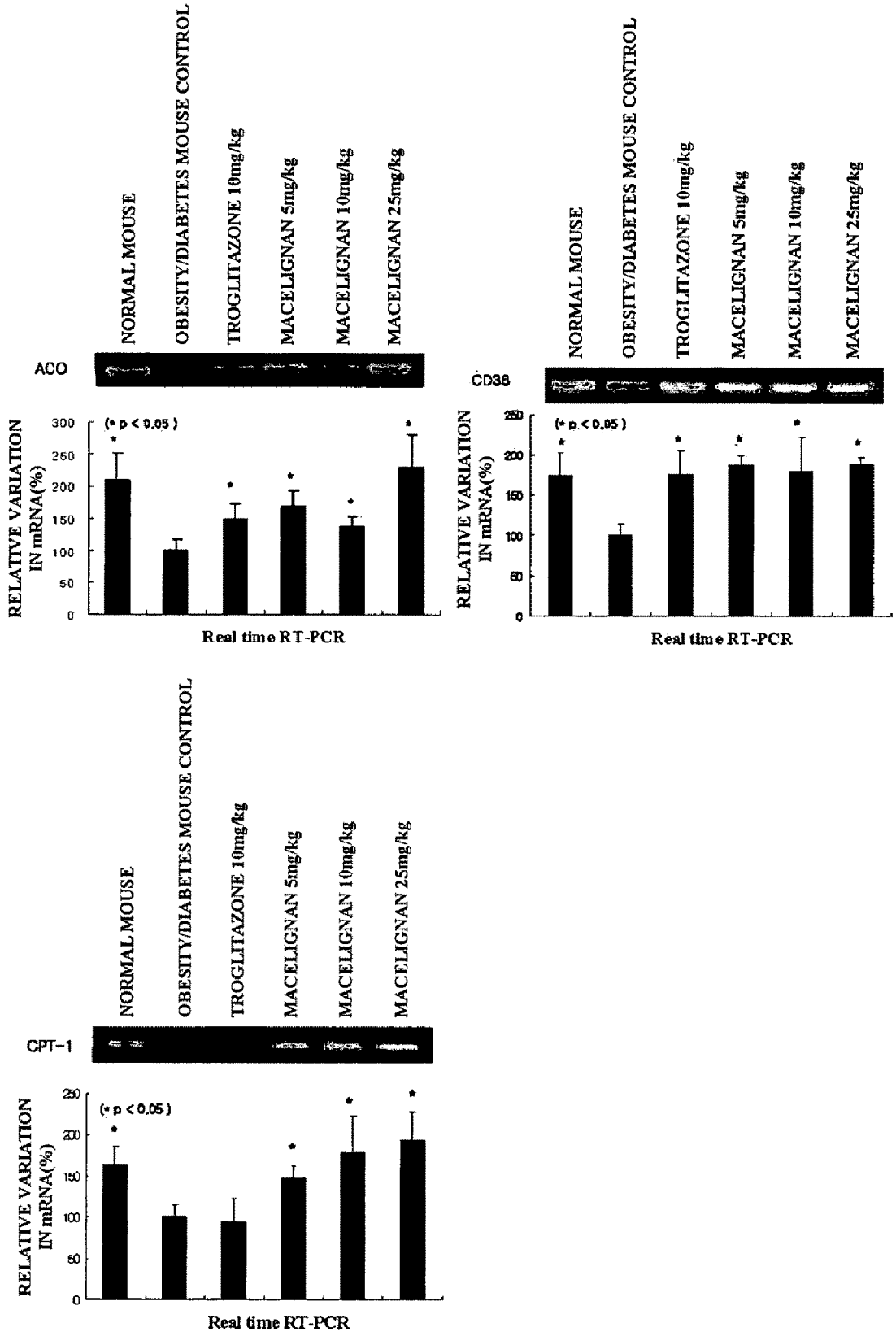
FIG. 26 is a result showing the effect of macelignan according to the present invention upon the expression of target genes of PPARα in the liver tissue of an obesity/diabetes mouse model;
A: CD36
B: ACO
C: CPT-1.

Finally, as shown in FIG. 26, mRNA expression of CD36, ACO and CPT-1 (target genes), whose expression is increased by PPARα, was significantly increased by the treatment with macelignan in all the test groups, when compared to the control (*, $p<0.05$). Herein, the graphs as shown in FIG. 26 are made by statistically processing the results obtained from each mouse used in Examples 5~8. Each photograph shown with the graphs illustrates the typical result. This indicates that macelignan can activate PPARα, and control the expression of target genes of PPARα, which play important roles in fatty acid oxidation, fat metabolism and inflammation inhibition, thereby reducing fats in blood and liver tissue. Therefore, it can be seen that macelignan is effective for preventing and treating hyperlipidemia, cardiovascular diseases and fatty liver mediated by PPAR.

<9-2> Determination of Expression of Target Genes of PPARγ

Liver tissue was removed from the test groups and the controls treated by oral administration in Examples 5~8. The liver tissue was homogenized in liquid nitrogen and the total RNA was isolated from the crushed tissues by using TRIZOL (Invitrogen, USA). The total RNA isolated as described above was determined and cDNA was synthesized by using reverse transcriptase at 42° C. for 20 minutes. The cDNA was subjected to RT-PCR by repeating the cycle of 95° C./1 minute, 56° C./30 seconds and 72° C./2 minutes thirty times with the following primers and Taq polymerase: primers for CD36 amplification (SEQ ID NO: 5 and SEQ ID NO: 6), primers for LPL amplification (SEQ ID NO: 13 and SEQ ID NO: 14), primers for ACS amplification (SEQ ID NO: 17 (AGCAGAGCTTCGCACGGC) and SEQ ID NO: 18 (TCTGCTGTTTCGCTGGGTCC) and primers for GyK amplification (SEQ ID NO: 19 (TCGAACCCGAGGATTTGTCT) and SEQ ID NO: 20 (AATTTCACTTTCCTCCGCATTAAT)). Expression of the genes was determined by real-time PCR.

Figure 27:
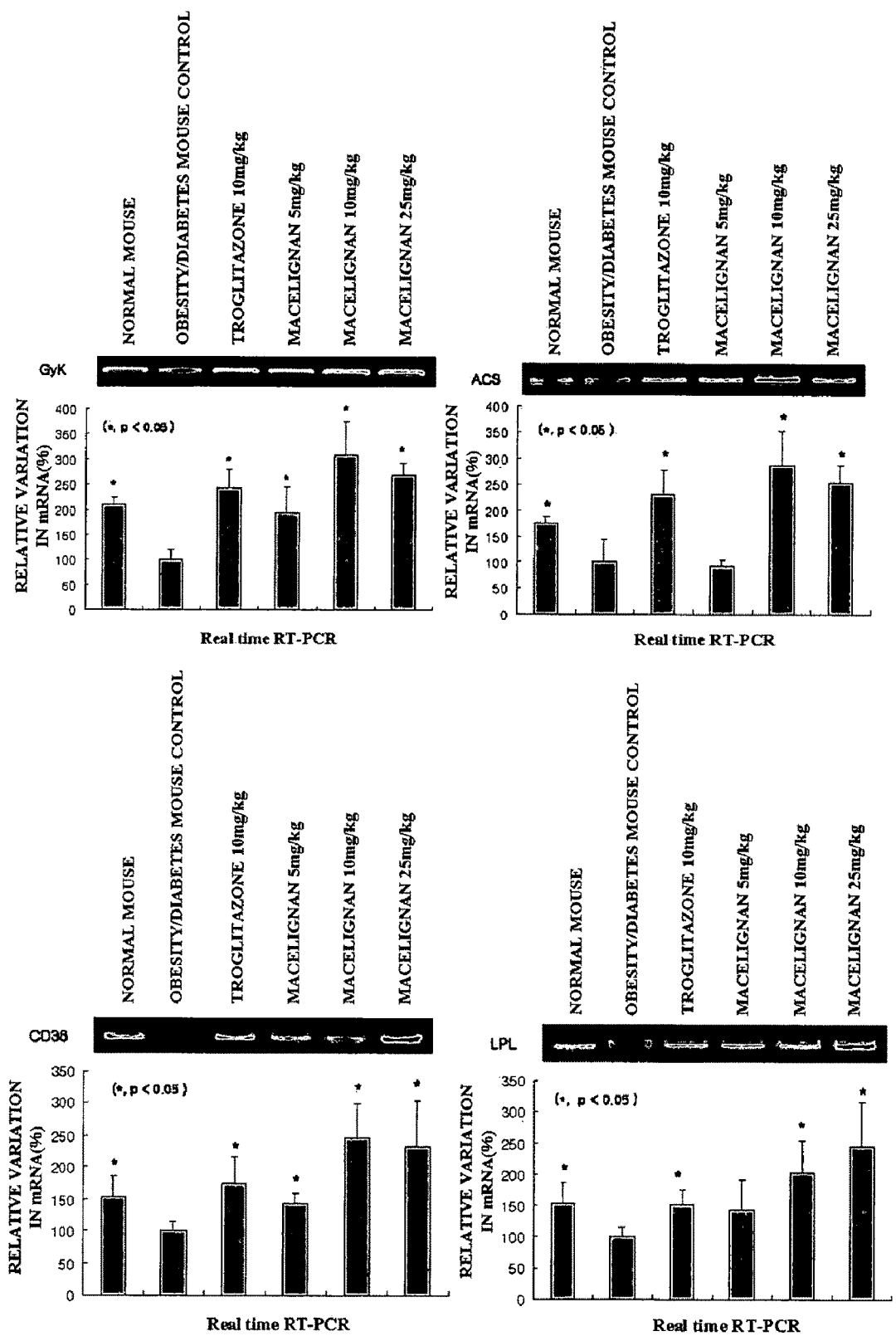
FIG. 27 is a result showing the effect of macelignan according to the present invention upon the expression of target genes of PPARδ in the liver tissue of an obesity/diabetes mouse model;
A: CD36
B: LPL
C: ACS
D: GyK.

Finally, as shown in FIG. 27, mRNA expression of CD36, LPL, ACS and GyK (target genes, expression of which is increased by PPARγ) was significantly increased by the treatment with macelignan in all the test groups, when compared to the control (*, $p<0.05$). Herein, the graphs as shown in FIG. 27 are made by statistically processing the results obtained from each mouse used in Examples 5~8. Each photograph shown with the graphs illustrates the typical result. This indicates that macelignan can activate PPARγ, and control the expression of target genes of PPARγ, playing important roles in sugar metabolism, thereby reducing blood sugar level and increasing insulin sensitivity. Therefore, it can be seen that macelignan is effective for preventing and treating diabetes mellitus and diabetic complication such as sugar metabolism-related diseases, mediated by PPAR.

Preparation Example 1

Preparation of Medicine Comprising Pharmaceutical Composition for Treating and Preventing Obesity, Hyperlipidemia and Cardiovascular Diseases According to the Present Invention <1-1> Preparation of Tablets First, 25 mg of macelignan according to the present invention was introduced into a U-shaped mixer together with 26 mg of lactose and 3.5 mg of Avicel (amorphous cellulose) as excipients for direct tablet making, 1.5 mg of sodium starch glyconate as a supplementary disintegrating agent, and 8 mg of L-HPC (low-hydroxypropylcellulose) as a binder, and then the mixture were mixed for 20 minutes. After the completion of the mixing, 1 mg of magnesium stearate as a lubricant was further added thereto, followed by mixing for additional 3 minutes. The mixture was subjected to a weight determination test and an anti-humidity test. Then, tablets were made from the mixture and coated with a film to provide finished tablets.

<1-2> Preparation of Syrup

Syrup comprising macelignan or a pharmaceutically acceptable salt thereof in an amount of 2% (W/V) as an active component was prepared by the following process: 2 g of an acid addition salt of macelignan according to the present invention, 0.8 g of saccharin and 25.4 g of sugar were dissolved into 80 g of hot water. After cooling the solution, 8.0 g of glycerin, 0.04 g of a perfume, 4.0 g of ethanol, 0.4 g of sorbic acid and an adequate amount of distilled water were mixed with the solution. Water was added to the resultant mixture to the final volume of 100 ml.

<1-3> Preparation of Capsule

First, 50 mg of macelignan according to the present invention, 50 mg of lactose, 46.5 mg of starch, 1 mg of talc and an adequate amount of magnesium stearate were mixed. Then, the mixture was filled into hard gelatin capsules to provide finished capsules.

<1-4> Preparation of Injection Solution

An injection solution comprising 10 mg of the active component was prepared by the following process: 1 g of hydrochloride salt of macelignan according to the present invention, 0.6 g of sodium chloride and 0.1 g of ascorbic acid were dissolved in distilled water to the final volume of 100 ml. The solution was introduced into ampoules, and the ampoules were heated and sterilized at 120° C. for 30 minutes.

INDUSTRIAL APPLICABILITY

As can be seen from the foregoing, macelignan according to the present invention functions as a ligand of PPAR and activates PP AR, so that it has the effect of preventing and treating PPAR-mediated diseases. Therefore, macelignan according to the present invention is useful for preventing and treating PPAR-mediated diseases such as diabetes mellitus and diabetic complications.

The invention claimed is:

1. A method for treating a PPAR-mediated disease, which comprises administering to a subject in need thereof an effective amount of macelignan represented by the following Formula (I):

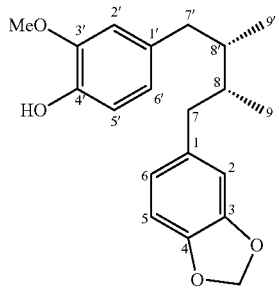

or a pharmaceutically acceptable salt thereof;

wherein the PPAR-mediated disease is selected from the group consisting of: NIDDM (non-insulin-dependent diabetes mellitus), hyperinsulinemia, obesity, hyperglycemia, hyperlipidemia, syndrome X, hypercholesterolemia, hyperlipoproteinemia, insulin resistance, dysmetabolic syndrome, impaired glucose homeostasis, impaired glucose tolerance, and hypertriglyceridemia.

2. The method according to claim 1, wherein the subject is a human.

3. The method according to claim 1, wherein the PPAR is PPARα or PPARγ.

* * * * *

SEQUENCE LISTING

<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: PPARa forward
<400> SEQUENCE: 1
cttggatccg aacatgacat a                                              21

<210> SEQ ID NO 2
<211> LENGTH: 19
<212> TYPE: DNA
<213> ORGANISM: Artificial Sequence
<220> FEATURE:
<223> OTHER INFORMATION: PPARa reverse
<400> SEQUENCE: 2
tggggtacct gtggctgat                                                 19

<210> SEQ ID NO 3
<211> LENGTH: 23
<212> TYPE: DNA
<213> ORGANISM: Artificial Sequence
<220> FEATURE:
<223> OTHER INFORMATION: PPARr forward
<400> SEQUENCE: 3
tcggtttaag attcatcttt att                                            23

<210> SEQ ID NO 4
<211> LENGTH: 24
<212> TYPE: DNA
<213> ORGANISM: Artificial Sequence
<220> FEATURE:
<223> OTHER INFORMATION: PPARr reverse
<400> SEQUENCE: 4
gtctccggta ccttgatcac ctgc                                           24

<210> SEQ ID NO 5
<211> LENGTH: 19
<212> TYPE: DNA
<213> ORGANISM: Artificial Sequence
<220> FEATURE:
<223> OTHER INFORMATION: CD36 forward
<400> SEQUENCE: 5
cggcgatgag aaagcagaa                                                 19

<210> SEQ ID NO 6
<211> LENGTH: 17
<212> TYPE: DNA
<213> ORGANISM: Artificial Sequence
<220> FEATURE:
<223> OTHER INFORMATION: CD36 reverse
<400> SEQUENCE: 6
caaccaggcc caggagc                                                   17

<210> SEQ ID NO 7
<211> LENGTH: 23
<212> TYPE: DNA

```
<213> ORGANISM: Artificial Sequence
<220> FEATURE:
<223> OTHER INFORMATION: CPT-1 forward

<400> SEQUENCE: 7
agacggtgga acagaggctg aag                                                23

<210> SEQ ID NO 8
<211> LENGTH: 27
<212> TYPE: DNA
<213> ORGANISM: Artificial Sequence
<220> FEATURE:
<223> OTHER INFORMATION: CPT-1 reverse

<400> SEQUENCE: 8
tgagaccaaa caaagtgatg atgtcag                                            27

<210> SEQ ID NO 9
<211> LENGTH: 21
<212> TYPE: DNA
<213> ORGANISM: Artificial Sequence
<220> FEATURE:
<223> OTHER INFORMATION: PDK4 forward

<400> SEQUENCE: 9
tcaaatcaaa atagccttcc c                                                  21

<210> SEQ ID NO 10
<211> LENGTH: 19
<212> TYPE: DNA
<213> ORGANISM: Artificial Sequence
<220> FEATURE:
<223> OTHER INFORMATION: PDK4 reverse

<400> SEQUENCE: 10
ataagttaag tgggcctgg                                                     19

<210> SEQ ID NO 11
<211> LENGTH: 21
<212> TYPE: DNA
<213> ORGANISM: Artificial Sequence
<220> FEATURE:
<223> OTHER INFORMATION: ACO forward

<400> SEQUENCE: 11
gggcatggct attctcattg c                                                  21

<210> SEQ ID NO 12
<211> LENGTH: 27
<212> TYPE: DNA
<213> ORGANISM: Artificial Sequence
<220> FEATURE:
<223> OTHER INFORMATION: ACO reverse

<400> SEQUENCE: 12
cgaacaaggt caacagaagt taggttc                                            27

<210> SEQ ID NO 13
<211> LENGTH: 20
<212> TYPE: DNA
<213> ORGANISM: Artificial Sequence
<220> FEATURE:
<223> OTHER INFORMATION: LPL forward

<400> SEQUENCE: 13
tatccgcgtg attgcagaga                                                    20
```

<210> SEQ ID NO 14
<211> LENGTH: 25
<212> TYPE: DNA
<213> ORGANISM: Artificial Sequence
<220> FEATURE:
<223> OTHER INFORMATION: LPL reverse

<400> SEQUENCE: 14
agagagtcga tgaagagatg aatgg                                              25

<210> SEQ ID NO 15
<211> LENGTH: 21
<212> TYPE: DNA
<213> ORGANISM: Artificial Sequence
<220> FEATURE:
<223> OTHER INFORMATION: PEPCK forward

<400> SEQUENCE: 15
caggcggctg aagaagtatg a                                                  21

<210> SEQ ID NO 16
<211> LENGTH: 21
<212> TYPE: DNA
<213> ORGANISM: Artificial Sequence
<220> FEATURE:
<223> OTHER INFORMATION: PEPCK reverse

<400> SEQUENCE: 16
aaccgtcttg ctttcgatcc t                                                  21

<210> SEQ ID NO 17
<211> LENGTH: 19
<212> TYPE: DNA
<213> ORGANISM: Artificial Sequence
<220> FEATURE:
<223> OTHER INFORMATION: ACS forward

<400> SEQUENCE: 17
agcagagctt cgcagcggc                                                     19

<210> SEQ ID NO 18
<211> LENGTH: 21
<212> TYPE: DNA
<213> ORGANISM: Artificial Sequence
<220> FEATURE:
<223> OTHER INFORMATION: ACS reverse

<400> SEQUENCE: 18
tctgctgttt tcgctgggtc c                                                  21

<210> SEQ ID NO 19
<211> LENGTH: 20
<212> TYPE: DNA
<213> ORGANISM: Artificial Sequence
<220> FEATURE:
<223> OTHER INFORMATION: GyK forward

<400> SEQUENCE: 19
tcgaacccga ggatttgtct                                                    20

<210> SEQ ID NO 20
<211> LENGTH: 24
<212> TYPE: DNA
<213> ORGANISM: Artificial Sequence
<220> FEATURE:
<223> OTHER INFORMATION: GyK reverse

```
<400> SEQUENCE: 20
aatttcactt tcctccgcat taat                                          24
```